US010441262B2

(12) United States Patent
Palomar-Moreno et al.

(10) Patent No.: US 10,441,262 B2

(45) Date of Patent: Oct. 15, 2019

(54) RETRIEVABLE ACCESS VALVE

(71) Applicant: BOSTON SCIENTIFIC LIMITED, Hamilton (BM)

(72) Inventors: Javier Palomar-Moreno, Galway (IE); Emma J. Mooney, Galway (IE); Michael Walsh, Galway (IE); Martyn G. Folan, Galway (IE); Gary Duffy, County Kildare (IE)

(73) Assignee: BOSTON SCIENTIFIC LIMITED, Hamilton (BM)

( * ) Notice: Subject to any disclaimer, the term of this patent is extended or adjusted under 35 U.S.C. 154(b) by 0 days.

(21) Appl. No.: 15/927,637

(22) Filed: Mar. 21, 2018

(65) Prior Publication Data

US 2018/0271510 A1 Sep. 27, 2018

Related U.S. Application Data

(60) Provisional application No. 62/475,164, filed on Mar. 22, 2017.

(51) Int. Cl.

*A61B 17/02* (2006.01)
*A61M 39/02* (2006.01)

(Continued)

(52) U.S. Cl.

CPC ...... *A61B 17/0218* (2013.01); *A61B 17/0293* (2013.01); *A61M 39/0208* (2013.01);

(Continued)

(58) Field of Classification Search

CPC ............ A61B 17/0218; A61B 17/0293; A61B 2090/3966; A61B 2017/00867;

(Continued)

(56) References Cited

U.S. PATENT DOCUMENTS 5,238,004 A 8/1993 Sahatjian et al.
6,264,700 B1 7/2001 Kilcoyne et al.

(Continued)

FOREIGN PATENT DOCUMENTS

EP 1205211 A1 5/2002
EP 1550478 A1 7/2005

(Continued)

OTHER PUBLICATIONS

Asheim, P., et al., "Intraperitoneal fluid therapy: an alternative to intravenous treatment in a patient with limited vascular access," Anaesthesia, 2006, 61, pp. 502-504.

(Continued)

*Primary Examiner* — Pedro Philogene
*Assistant Examiner* — David C Comstock
(74) *Attorney, Agent, or Firm* — Seager, Tufte & Wickhem, LLP

(57) ABSTRACT

Medical devices and methods for making and using medical devices are disclosed. An example medical device may include an access valve that may be retrieved after implantation. The access valve may include a frame having a lumen, a self-expandable member extending through the lumen, and an elastic membrane extending through the lumen and a second end of the frame to releasably seal the lumen. The access valve may releasably attach to a wall of a patient and releasably seal an opening through the wall. The access valve may be attached to the wall by placing the frame adjacent the wall, extending the self-expandable member through the opening in the wall, and expanding the self-expandable member such that the self-expandable member applies a first force against the wall and a second force opposite the first force against the frame to sandwich the wall between the self-expandable member and the frame.

19 Claims, 18 Drawing Sheets

(51) Int. Cl.

| | |
|---|---|
| *A61M 5/168* | (2006.01) |
| *A61B 90/00* | (2016.01) |
| *A61B 17/00* | (2006.01) |
| *A61M 27/00* | (2006.01) |

(52) U.S. Cl.

CPC ............... *A61B 2017/00867* (2013.01); *A61B 2017/0225* (2013.01); *A61B 2017/0287* (2013.01); *A61B 2090/3966* (2016.02); *A61M 5/16881* (2013.01); *A61M 27/002* (2013.01); *A61M 2039/0223* (2013.01); *A61M 2039/0229* (2013.01); *A61M 2039/0232* (2013.01)

(58) Field of Classification Search

CPC ... A61B 2017/0255; A61B 2017/0287; A61M 39/0208; A61M 5/16881; A61M 27/002; A61M 2039/0223; A61M 2039/0229; A61M 2039/0232

USPC .................................. 600/208; 606/153, 156

See application file for complete search history.

(56) References Cited

U.S. PATENT DOCUMENTS

| | | | | |
|---|---|---|---|---|
| 6,508,803 | B1 | 1/2003 | Horikawa et al. | |
| 6,544,291 | B2 | 4/2003 | Taylor | |
| 6,958,037 | B2 * | 10/2005 | Ewers ...................... | A61B 1/32 600/208 |
| 8,834,361 | B2 * | 9/2014 | Hashiba ............. | A61B 17/3421 600/206 |
| 9,333,332 | B2 | 5/2016 | Eisenkolb et al. | |
| 2005/0137518 | A1 * | 6/2005 | Biggs ................... | A61B 17/064 604/8 |
| 2010/0191166 | A1 | 7/2010 | Phillips et al. | |
| 2010/0234876 | A1 | 9/2010 | Watson | |
| 2010/0261974 | A1 * | 10/2010 | Shelton, IV ....... | A61B 17/3423 600/208 |
| 2010/0274223 | A1 | 10/2010 | Teitelbaum et al. | |
| 2010/0286484 | A1 * | 11/2010 | Stellon ............... | A61B 17/3423 600/208 |
| 2012/0157781 | A1 * | 6/2012 | Kleyman ........... | A61B 17/3423 600/208 |
| 2014/0012180 | A1 | 1/2014 | Levin et al. | |
| 2015/0272559 | A1 * | 10/2015 | Rowe ................. | A61B 17/0293 600/208 |
| 2016/0143739 | A1 | 5/2016 | Horgan et al. | |
| 2017/0028176 | A1 | 2/2017 | Dam et al. | |

FOREIGN PATENT DOCUMENTS

| | | |
|---|---|---|
| EP | 2329796 A2 | 6/2011 |
| EP | 2351595 A1 | 8/2011 |

OTHER PUBLICATIONS

"Management of Ascites in Ovarian Cancer Patients," Royal College of Obstetricians & Gynaecologists, Scientific Impact Paper No. 45, Nov. 2014 (6 pgs).

Yonemura, Y., et al., "Recent advances in the treatment of peritoneal dissemination of gastrointestinal cancers by nucleoside antimetabolites," Cancer Sci, Jan. 2007, vol. 98, No. 1, 11-18.

International Search Report and Written Opinion dated Jun. 25, 2018 for International Application No. PCT/US2018/023577.

* cited by examiner

F1
F2
26
14a
14b
30
15
20
32
14
13
20
20
12
22
16
18
12a
10
12b
24
28

F1
F2
10
12
12a
12b
13
14
14a
14b
15
16
18
20
22
24
26
28
30
32
34
36

4
2
10
12
22
26
14
50
20
46
48
20
18
12a
12b
24

RETRIEVABLE ACCESS VALVE

CROSS REFERENCE TO RELATED APPLICATIONS

The present application claims the benefit of and priority to U.S. Provisional Patent Application Ser. No. 62/475,164, filed Mar. 22, 2017, the disclosure of which is incorporated herein by reference.

TECHNICAL FIELD

The present disclosure pertains to medical devices, and methods for manufacturing and using medical devices. More particularly, the present disclosure pertains to implantable medical devices including access valves.

BACKGROUND

A wide variety of medical devices have been developed for medical use, for example, for use in accessing body cavities. Some of these devices may include guidewires, catheters, endoscopes, needles, valves, and delivery devices and/or systems used for delivering such devices. These devices are manufactured by any one of a variety of different manufacturing methods and may be used according to any one of a variety of methods. Of the known medical devices and methods, each has certain advantages and disadvantages.

BRIEF SUMMARY

This disclosure provides, design, material, manufacturing method, and use alternatives for medical devices. In a first aspect, an access valve may comprise a frame having a lumen extending along a length of the frame from a first end of the frame to a second end of the frame, a self-expandable member extending through the lumen of the frame and having a first end proximal of the first end of the frame and a second end distal of the second end of the frame, and an elastic membrane extending through the lumen and through the second end of the frame to releasably seal the lumen.

In addition or alternative, and in a second aspect, the elastic membrane may be secured to the self-expandable member.

In addition or alternative, and in a third aspect, the self-expandable member may have a collapsed configuration and an expanded configuration and when the self-expandable member is in the expanded configuration, the self-expandable member may apply an axially compressive force to the frame.

In addition or alternative, and in a fourth aspect, the frame may have an interior surface defining the lumen and the interior surface may taper from the first end to the second end of the frame.

In addition or alternative, and in a fifth aspect, the frame may have a conical first portion and a second portion extending radially outward from the conical first portion.

In addition or alternative, and in a sixth aspect, the second portion may have a first side facing the conical first portion and a second side opposite the first side; and a sealing membrane may be secured to the second side of the second portion.

In addition or alternative, and in a seventh aspect, the second portion of the frame may be configured to articulate with respect to the conical first portion of the frame.

In addition or alternative, and in an eighth aspect, the elastic membrane may comprise a compressible foam.

In addition or alternative, and in a ninth aspect, the frame may be substantially rigid against radial and axial forces acting on the frame from the self-expandable member.

In addition or alternative, and in a tenth aspect, the self-expandable member may be formed from a metal braid.

In addition or alternative, and in an eleventh aspect, the access valve may further comprise a retrieval flange connected to the self-expandable member and extending proximal of the frame.

In addition or alternative, and in a twelfth aspect, a positioning system for positioning an access valve against a bodily wall of a patient may comprise a delivery sheath, a valve comprising a frame having a first end, a second end, and a lumen extending from the first end to the second end, a self-expandable member extending through the frame and having a first end proximal of the first end of the frame and a second end distal of the second end of the frame, and an elastic membrane extending through the lumen to releasably seal the lumen, wherein the delivery sheath may be configured to be inserted through the lumen of the frame while covering the self-expandable member to maintain the self-expandable member in a collapsed configuration and may be retractable to allow the self-expandable member to expand to an expanded configuration to allow the elastic membrane to releasably seal the lumen.

In addition or alternative, and in a thirteenth aspect, the positioning system may further comprise a guide wire, and the valve and the delivery sheath may extend over the guide wire.

In addition or alternative, and in a fourteenth aspect, once the delivery sheath is retracted, the self-expandable member may expand radially and axially contract.

In addition or alternative, and in a fifteenth aspect, the valve may further comprise a retrieval flange extending proximal of the frame.

In addition or alternative, and in a sixteenth aspect, a method of using an access valve may comprise advancing a guide wire to a target area on a bodily wall of a patient, puncturing through the bodily wall of the patient at the target area, advancing an access valve to the target area, positioning a frame of the access valve against the bodily wall at the target area, extending a self-expandable member of the access valve through the frame and the puncture in the bodily wall, retracting a delivery sheath covering the self-expandable member to allow the self-expandable member to expand to an expanded configuration, and wherein the self-expandable member in the expanded configuration applies axial compressive forces against the bodily wall of the patient and the frame to secure the frame against the bodily wall.

In addition or alternative, and in a seventeenth aspect, an elastic membrane of the access valve may releasably seal the access valve when the self-expandable member is in the expanded configuration and extending through the frame.

In addition or alternative, and in an eighteenth aspect, the method may further comprise inserting a catheter into the elastic membrane and advancing the catheter through the elastic membrane to access a distal side of the bodily wall.

In addition or alternative, and in a nineteenth aspect, the method may further comprise inserting an endoscope into a body cavity at least partially defined by the bodily wall of the patient, and the access valve may be advanced through the inserted endoscope to the target area.

In addition or alternative, and in a twentieth aspect, the method may further comprise grasping a retrieval flange connected to the self-expandable member and extending proximal of the frame, and withdrawing the self-expandable member into a retrieval sheath to place the self-expandable member in a collapsed configuration for removing the access valve from the patient.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
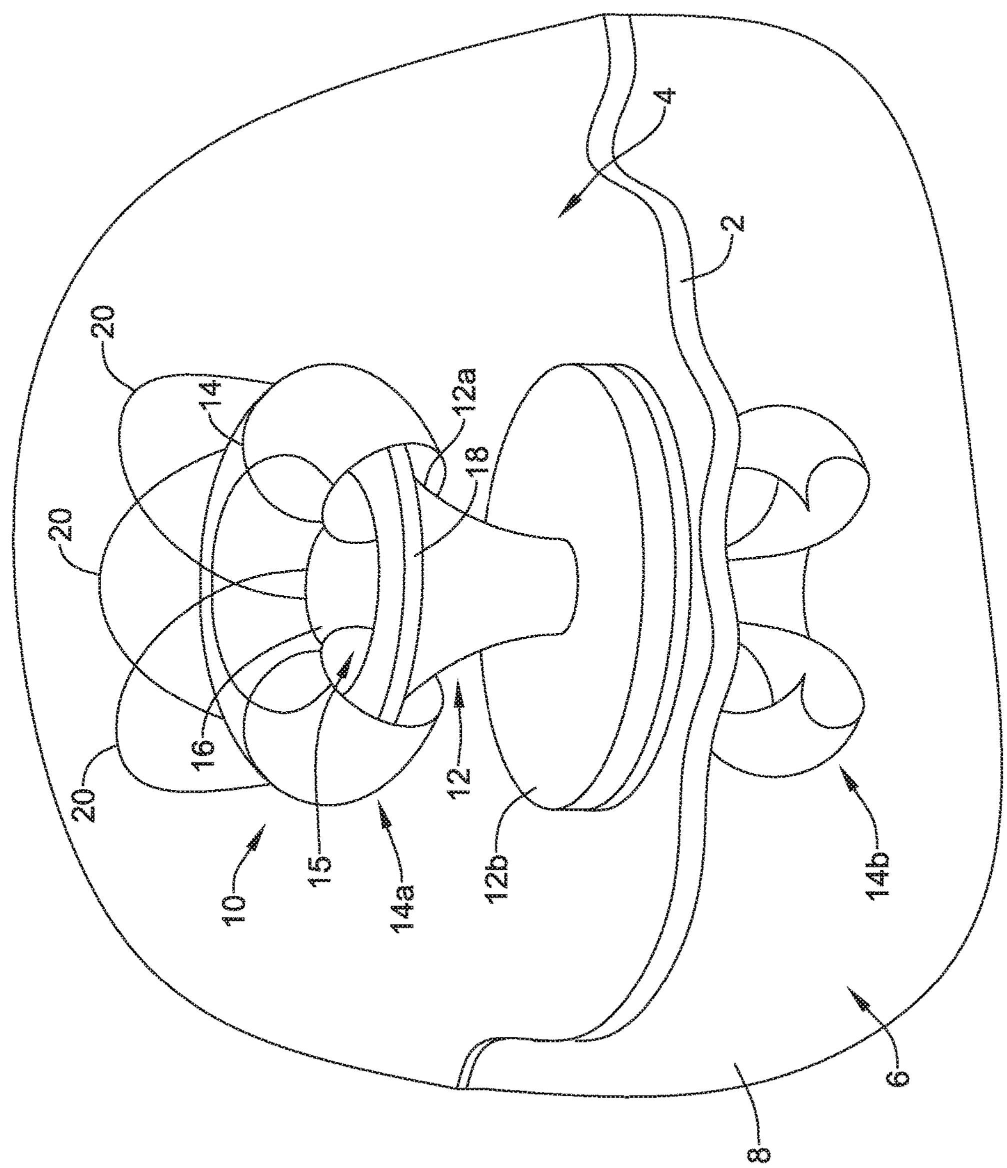
FIG. 1 is a partial cross-sectional perspective view illustrating an example valve implanted on a wall of a stomach.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term “about”, whether or not explicitly indicated. The term “about” generally refers to a range of numbers that one of skill in the art would consider equivalent to the recited value (e.g., having the same function or result). In many instances, the terms “about” may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms “a”, “an”, and “the” include plural referents unless the content clearly dictates otherwise. As used in this specification and the appended claims, the term “or” is generally employed in its sense including “and/or” unless the content clearly dictates otherwise.

It is noted that references in the specification to “an embodiment”, “some embodiments”, “other embodiments”, etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Periodic infusions to and/or drainages from a body may be facilitated with a valve (e.g., a permanent or temporary valve), especially when an access point may be critical and/or difficult to locate. In some cases, endoscopic micro-catheters and/or other micro-catheters may be utilized with a valve to facilitate infusions and/or drainages within a patient’s body. An access valve that may be implantable and/or retrievable, as disclosed here, may be used in procedures with endoscopes, micro-catheters, and/or other delivery, investigative, and/or treatment devices to facilitate infusions and/or drainages within a patient’s body.

In some cases, the access valve may be used in infusion procedures. In an example, infusions may be utilized to treat peritoneal dissemination by providing (e.g., injecting) replacement fluids to the peritoneal cavity. Specific targets on a stomach wall of a patient and/or a descending colon wall may be suitable locations to implant a removable valve, such as the one disclosed herein. The removable valve may be implanted via endoscopy and/or colonoscopy and once implanted, may facilitate periodic infusions into the peritoneal cavity without leakage across the valve when the infusion is not being used.

In some cases, the access valve may be used instead of or in replacement of anastomosis devices. Anastomosis devices may be used to facilitate transgastric or transduodenal endoscopic drainage of symptomatic pancreatic pseudocysts that may be, for example, adherent to a gastric or bowel wall. The anastomosis devices are temporary devices intended for implantation up to about sixty (60) days and should be removed upon confirmation of pseudocyst resolution. However, implanted anastomosis devices may leak gastric acid. The removable valve disclosed herein may be to replace anastomosis devices used for transgastric or transduodenal drainage, as the removable valve may remain sealed until a force is received (e.g., from an endoscope, drainage catheter, or other medical device) to open the valve on demand.

As such, the disclosed retrievable valve may be suitable for providing access through a wall and sealing that access when the access is not needed. In some cases, the valve may be used at locations along a wall that did not previously have an orifice, but this is not required. When deployed, the retrievable valve may sandwich a wall between a base of a frame (e.g., where the base of the frame may be a second portion of the frame that extends radially outward from a vertex of a conical first portion of the frame and where the frame of the valve may include the conical first portion to channel and/or direct a medical device through the valve) and an expandable member extending through the wall to secure the valve at a location along the wall. When the wall includes an orifice covered by the valve, securing the valve to the wall may allow for controlling the exchange of fluid through that orifice by selective opening of the valve. Such a valve may facilitate periodic infusion of therapeutics and drainage of a cavity over time and over a plurality of procedures, where the valve may be implanted on a first procedure and subsequent procedures may access the valve as needed. In some cases, the valve may be applied to a bodily wall (e.g., a wall interior of a body cavity (e.g., stomach, colon, or other cavity) and/or a wall exterior of a body cavity (e.g., on skin adjacent a stomach, a peritoneal cavity, or at any other location) of a patient.

FIG. 1 is a schematic view of a valve 10 (e.g., the valve 10 with a portion of an expandable member 14 cut a way to illustrate other features of the valve 10) secured to a wall 2 between a stomach 4 and a peritoneal cavity 6 defined as a space between the wall 2 and peritoneum 8. Although FIG. 1 depicts the valve 10 positioned against the wall 2 within the stomach 4, the valve 10 may be positioned against the wall 2 within the peritoneal cavity 6, and/or positioned at any location within the body or on an exterior surface of the body. As shown in FIG. 1, the valve 10 may include a frame 12, an expandable member 14 extending through the frame 12, and a valve membrane 16 extending through the frame 12.

The frame 12 of the valve 10 may take on any shape or configuration. In some instances, the frame 12 may have a first portion 12*a* and a second portion 12*b*. The first portion 12*a* and the second portion 12*b* of the frame 12 may be formed from a single piece of material or formed from two or more pieces of material connected together. In some cases, the first portion 12*a* of the frame may take on a funnel shape or conical shape and the second portion 12*b* may take on a disc shape (e.g., a pressing ring or other feature). The funnel or conical shape of the first portion 12*a* of the frame 12 may be a shape of an exterior surface of the first portion 12*a*, a shape of an interior surface of the first portion 12*a*, or the shape of the interior and exterior surfaces of the first portion 12*a*. The second portion 12*b* of the frame 12 may be a base configured to face or be placed adjacent a wall (e.g., the wall 2 of the stomach 4 or other wall) and spread a load applied to the frame 12 away from an opening in the wall. Other configurations of the first portion 12*a* and the second portion 12*b* of the frame 12 that are suitable for receiving medical devices and spreading loads applied to the frame by the received medical devices may be utilized.

The expandable member 14 may extend through the frame 12 and when in an expanded configuration (as shown in FIG. 1), the expandable member 14 may extend proximal of a proximal end of the frame 12 and distal of a distal end of the frame 12. In some cases, a first end 14*a* of the expandable member 14 may extend around a proximal end of the frame 12 (e.g., a lip 18 or other part of the proximal end of the frame 12). The first end 14*a* of the expandable member 14 and a second end 14*b* of the expandable member 14 may extend axially inward and in some instances, the first end 14*a* and the second end 14*b* of the expandable member 14 may form toroidal shapes or shapes that facilitate applying axially inward (e.g., compressive) forces on the frame 12.

Further, the expandable member 14 may include one or more retrieval members 20 connected to and/or extending proximally relative to the second portion 12*b* of the frame 12. The retrieval members 20 may be any feature configured to be engaged by a retrieval device. In some cases, the retrieval members 20 may be flanges, loops, balls, and/or other features extending from the expandable member 14. In one example, the retrieval members 20 may be made from the same structure used to form the expandable member 14. Alternatively, the retrieval members 20 may be made from one or more other materials and connected to the expandable member 14 in one or more manners.

As seen in FIG. 1, the valve membrane 16 may extend within the expandable member 14 and the frame 12. Although not shown in FIG. 1, the valve membrane 16 may extend through a distal end of the frame 12 and to close the valve 10 when the valve is not opened in response to a positive force.

Figure 2:
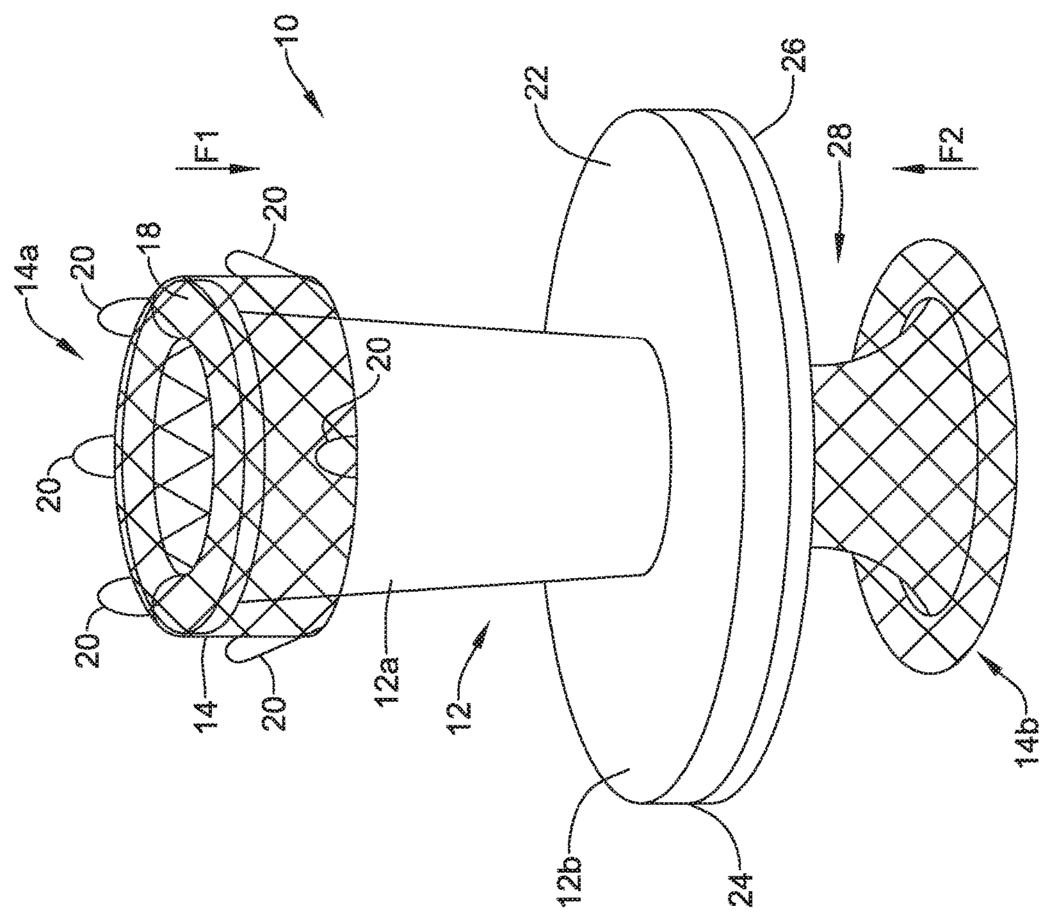
FIG. 2 is an elevation view illustrating an example valve.

FIG. 2 is a schematic side or elevation view of the valve 10 with the expandable member 14 expanded within the frame 12. As can be seen, the first portion 12*a* of the frame 12 may have an outer diameter that tapers toward the second portion 12*b* of the frame 12. The second portion 12*b* of the frame 12 may have a proximal side 22 facing the first portion 12*a* of the frame 12 and a distal side 24 facing a second end 14*b* of the expandable member 14.

The expandable member 14 may apply axial and/or radial forces on the frame when the expandable member 14 is in an expanded configuration. In some cases, the first end 14*a* of the expandable member 14 may self-expand within the frame 12 such that the expandable member 14 exerts an axially compressive force in a first direction, F1. In one example, the first end 14*a* of the expanded expandable member 14 may be configured to expand in such a manner that it flips on itself and extend distally toward the second portion of the frame. In such a configuration, the first end 14*a* of the expandable member 14 may apply a compressive force in the first direction, F1, toward a proximal end or other part of the frame 12. Further, when the expandable member 14 is in the expanded configuration, the retrieval members 20 may extend in a proximal direction and in some cases, proximally of a proximal end of the frame 12.

An axial space 28 may be located between a base membrane 26 and the second end 14*b* of the expandable member 14. The axial space 28 may be configured to receive a wall (e.g., the wall 2 of the stomach 4 or other wall) or other body structure. When a wall or other body structure is received within the axial space 28, the second end 14*b* may apply an axially compressive force in a second direction, F2, to compress the wall or the body structure between the second end 14*b* of the expandable member 14 and the base membrane 26 and/or the second side 24 of the second portion 12*b* of the frame 12. When both of the compressive force in the first direction, F1, and the force in the second direction, F2, are acting on the valve 10 (e.g., frame 12 and/or the features of the valve 10), the valve 10 may be secured to the wall or other body structure within the axial space 28.

Figure 3:
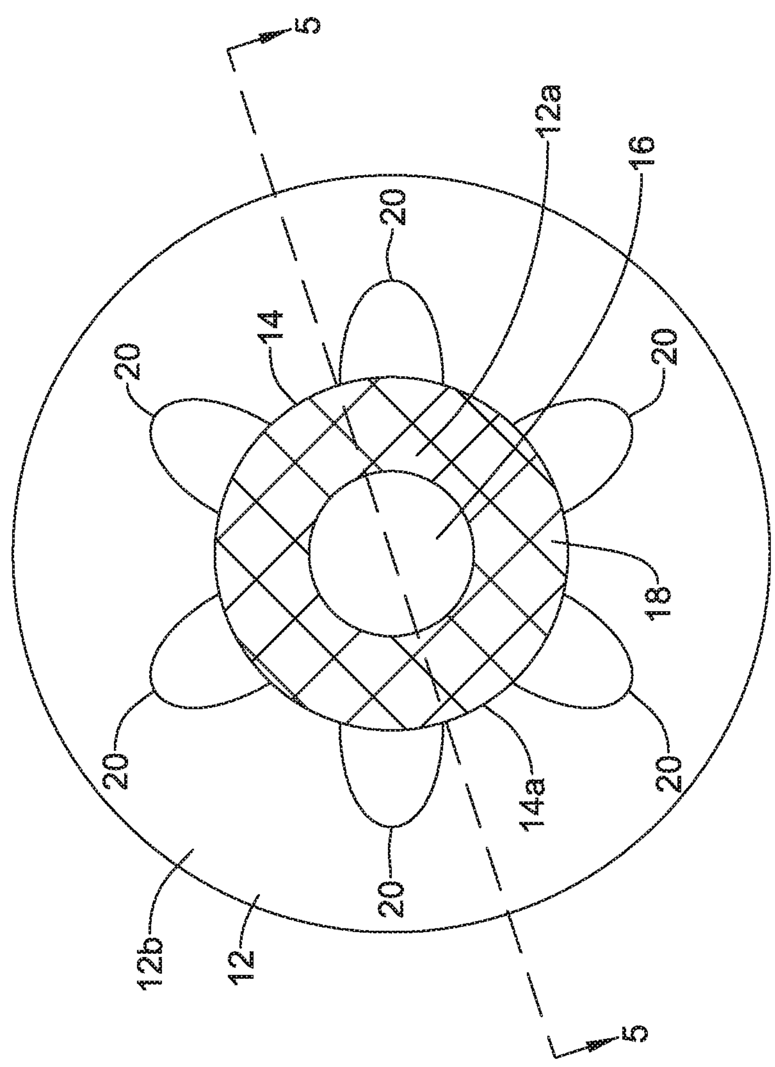
FIG. 3 is a top plan view illustrating the example valve of FIG. 2.

FIG. 3 is a schematic top plan view of the valve 10. As can be seen in FIG. 3, the retrieval members 20 may extend from the expandable member 14. Additionally or alternatively to the retrieval members 20 extending proximally relative to the frame 12, the retrieval members 20 may extend radially outward from the frame 12 to facilitate being engaged by a retrieval device.

Any number of retrieval members 20 may be utilized. Although six (6) retrieval members 20 are depicted in FIG. 3, the valve 10 may include one (1) retrieval member 20, two (2) retrieval members 20, three (3) retrieval members 20, four (4) retrieval members 20, five (5) retrieval members 20, ten (10) retrieval members 20, and/or any other number of retrieval members 20 facilitating removal of the valve 10 from a target location. The retrieval members 20 may be symmetrically or asymmetrically positioned around a circumference of the expandable member 14. In one example, as depicted in FIG. 3, the retrieval members 20 may form a ring around the expandable member 14

As seen in FIG. 3, the valve membrane 16 be within the frame 12 and the expandable member 14. The membrane may be biased to a closed position and opened in response to a positive force applied thereto, including but not limited to a force applied by a scope or catheter.

Figure 4:
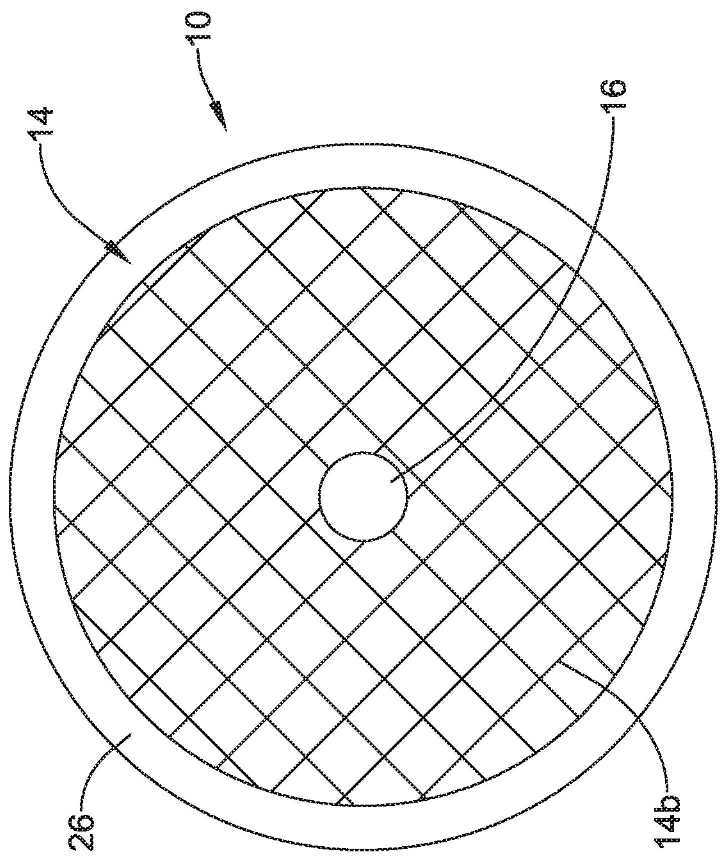
FIG. 4 is a bottom plan view illustrating the example valve of FIG. 2.

FIG. 4 is a schematic bottom plan view of the valve 10 with the expandable member 14 extending through the frame 12 and expanded within the frame 12. Similar to with the top view of FIG. 3, the valve membrane 16 may be seen in a closed position within the frame 12 and the expandable member 14.

Figure 5:
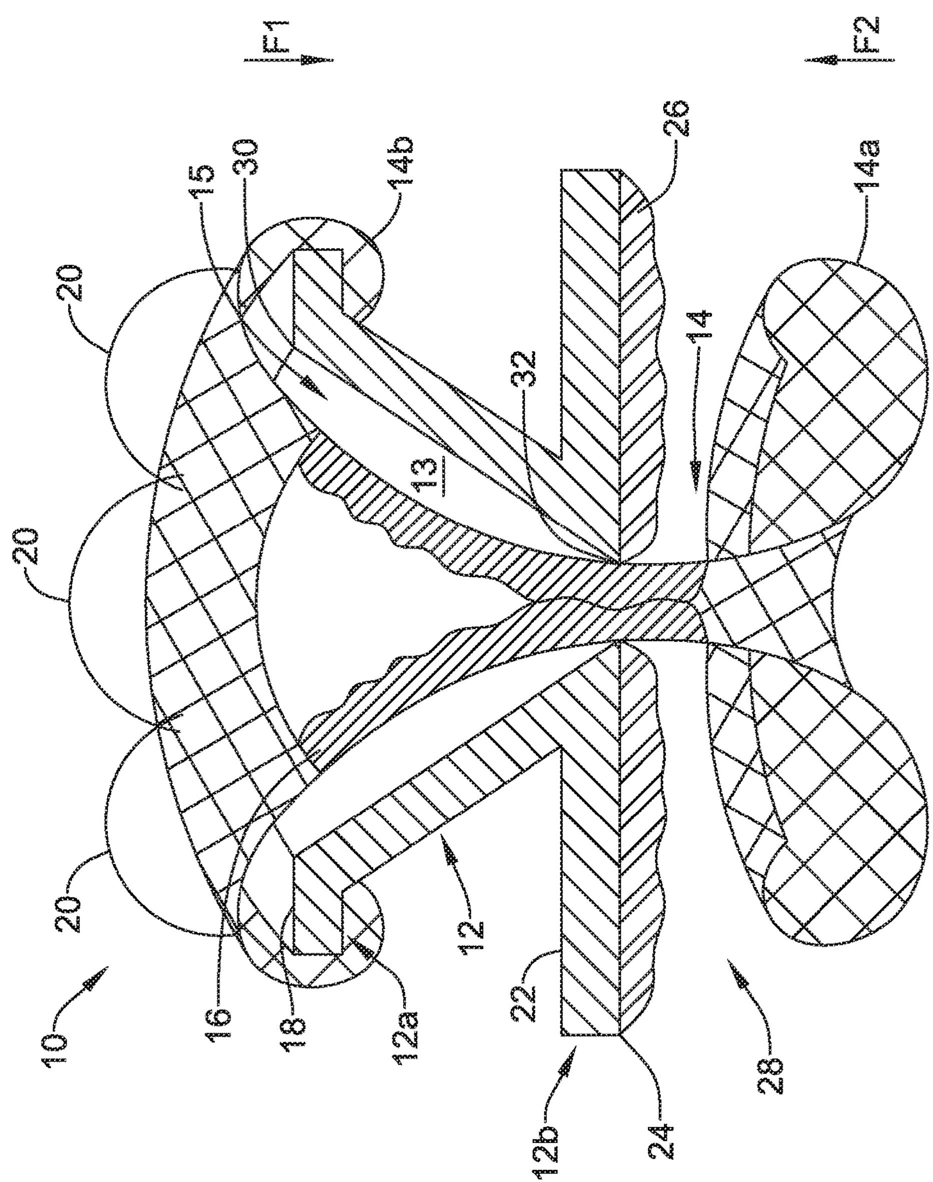
FIG. 5 is a cross-sectional view illustrating the example valve of FIG. 2, taken along line 5-5 in FIG. 3.

FIG. 5 is a schematic cross-sectional view take along line 5-5 in FIG. 3. In FIG. 5, the frame 12 is depicted as a single piece of material. However, as discussed above, the frame 12 may be formed from one or more pieces of material. In instances, when the frame 12 may be formed from more than one piece, the pieces of the frame 12 may be connected in any manner. In some instances, connecting the pieces of the frame 12 may include one or more example connecting mechanisms including, but not limited to, friction fit bonding, adhesive bonding, welding, thermal bonding, brazing, metallurgical stamping, pressing, etc. In one example, when the first portion 12*a* of the frame 12 may be a first piece of material and the second portion 12*b* of the frame 12 may be a second piece of material, the first portion 12*a* of the frame 12 may be connected to the second portion 12*b* of the frame through a welding connection or other connection.

In FIG. 5, the first portion 12*a* of the frame 12 includes a tapering inner diameter defined by an interior surface 13, where the inner diameter tapers from its widest at a first opening 30 (e.g., a proximal opening) of the frame 12 to its narrowest at a second opening 32 (e.g., a distal opening) of the frame 12. That is, the interior surface 13 may define a lumen 15, where, in some cases, the lumen 15 tapers from adjacent the first opening 30 to adjacent the second opening 32. Other configurations are contemplated and any inner diameter configuration for the frame 12 may be utilized that facilitates receiving elements (e.g., catheters, scopes, etc.) within the frame 12 and/or directing the received elements through the second opening 32 of the frame 12.

The frame 12 may be formed from any biocompatible material and may include one or more radiopaque materials. In some cases, the frame 12 may be formed from a rigid material to provide a rigid structure to the valve 10 that is rigid against radial and/or axial forces acting on the frame 12 from the self-expandable member 14 and/or against other forces acting on the frame 12. In one example, the frame 12 may be formed from a rigid medical grade stainless steel.

When the frame 12 is formed from a rigid material, the second portion 12*b* of the frame 12 may be configured to articulate with respect to the first portion 12*a* of the frame 12. The second portion 12*b* of the frame 12 may be configured to articulate in any manner with respect to the first portion 12*a* of the frame. In one example, the second portion 12*b* of the frame 12 may have a flexible hinge connection to the first portion 12*a* is of the frame 12. Alternatively, or in addition, a flexible and/or resilient material may be provided between the first portion 12*a* and the second portion 12*b* of the frame 12. Although examples of articulating configurations for the frame 12 are described, other articulating configurations are contemplated. Additionally, in some cases, the second portion 12*b* of the frame 12 may not articulate with respect to the first portion 12*b* of the frame 12.

As can be seen in the example of FIG. 5 and as discussed above, the first end 14*a* of the expandable member 14 may curl around (e.g., curl radially outward and distally) or otherwise engage a proximal end (e.g., the lip 18 or other proximal end feature of the frame 12) of the first portion 12*a* of the frame 12. Engaging the proximal end of the first portion 12*a* of the frame 12 may apply an axially compressive force in the first direction F1. Extending from the first end 14*a* of the expandable member 14, may be a conical portion that radially narrows (e.g., tapers) along the taper of the first portion 12*a* of the frame 12 and then radially expands after passing through the second portion 12*b* of the frame 12 and ends at the second end 14*b* of the expandable member 14. Further, as seen in FIG. 5, the second end 14*b* of the expandable member 14 may curl (e.g., curl radially outward and proximally) or otherwise extend radially outward and proximally toward the axial space 28. Thus, when a wall or other feature is received in the axial space 28, the valve 10 may be secured to the wall or other feature due to the axially compressive forces acting in the first direction F1 and the second direction F2.

The expandable member 14 may be formed from any biocompatible material and may include one or more radiopaque materials. In some cases, the expandable member 14 may be made from any self-expanding biocompatible material, including metals and/or polymers. In some cases, the expandable member 14 may be made from a metal tube, a metal scaffold, a metal knit, a metal wrap, a metal bobbinet, a metal braid, a metal mesh, a metal coil, a polymer tube, a polymer scaffold, a polymer knit, a polymer wrap, a to polymer bobbinet, a polymer braid, a polymer mesh, a polymer coil, combinations thereof, and/or one or more other materials and configurations. In one example configuration of the expandable member 14, the expandable member 14 may be formed from a braid of self-expanding metal (e.g., a self-expanding stent or other metal braid) that may be formed to expand from a cylindrical shape (e.g., in a delivery configuration) is to the shape depicted in FIG. 5 (e.g., an expanded configuration).

As shown in FIG. 5, the valve membrane 16 may extend through the second opening 32 in the frame 12 and close the valve at the second opening 32 of the frame 12, among other locations. In some cases, the valve membrane 16 may be secured to the expandable member 14 and as a result, the valve membrane 16 may expand and contract with the expandable member 14. When in the expanded configuration, the expandable member 14 may taper from the first end 14*a* to a location adjacent the second opening 32 of the frame 12 to have a proximal funnel shape and then radially expand from the location adjacent the second opening 32 to the second end 14*b* (e.g., a distal end) of the expandable member 14. Although the valve membrane 16 may or may not extend an entire length of the expandable member 14, the valve membrane 16 may take on a shape similar to the shape (e.g., the funnel shape) of the expandable member when it is expanded and extended through the second opening 32 of the frame 12.

In some case, the configuration of the expandable member 14 engaging the frame 12 may apply radially inward forces to the valve membrane 16 to bias the valve membrane 16 and the valve 10 to a closed position. Additionally or alternatively, a diameter of a combination of the expandable member 14 and the valve membrane 16 may be greater than a diameter of the second opening 32 of the frame 12 and, as a result, the frame 12 may act on the expandable member 14 and the valve membrane 16 to bias the valve membrane 16 and/or the valve 10 to the closed position.

The valve membrane 16 may be formed from any type of material that may be capable of being biased to seal an opening and that may be opened by applying a force to the material and may include one or more radiopaque materials. In some cases, the valve membrane 16 may be formed from a compressible material, a resilient material, a pliable material, and/or an elastic material. In one example, the valve membrane 16 may be formed from a silicone material, but other compressible and non-compressible materials are contemplated. Although the valve membrane 16 may be depicted as having a single layer, the valve membrane 16 may include two or more layers, as suitable for various applications. Further, the valve membrane 16 may take the form of a lining, foam, and/or other material applied to expandable member. The base membrane 26, which may be configured to provide a seal between the second portion 12*b* of the frame 12 and a wall is (e.g., the wall 2 or other wall) or other feature at which the valve 10 is to be placed, may be formed from the same material as the valve membrane or a different compressible, resilient, pliable, and/or elastic material.

The valve membrane 16 may be connected to the expandable member 14 in any manner. In some examples, the valve membrane 16 may be sewed to the expandable member 14 with sutures, the valve membrane 16 may be adhered to the expandable member 14 with one or more adhesives, the valve membrane 16 may encase a portion of the expandable member 14 and/or the valve membrane 16 may be secured to the expandable member 14 in one or more other manners.

Similar to the valve membrane 16, the base membrane 26 may be secured to the second portion 12*b* of the frame in any manner. In some examples, the base membrane 26 may be adhered to the second side 24 of the second portion 12*b* of the frame 12 with one or more adhesives and/or the base membrane 26 may be secured to the frame 12 in one or more other manners.

As indicated above, the valve 10 may include radiopaque materials. When the valve 10 includes radiopaque materials, a location of the valve 10 within an implant area may be readily viewed due to the radiopaque nature of the valve. This may be particularly useful, when locating a valve 10 that has already been implanted for a procedure and/or for removal.

Figure 6:
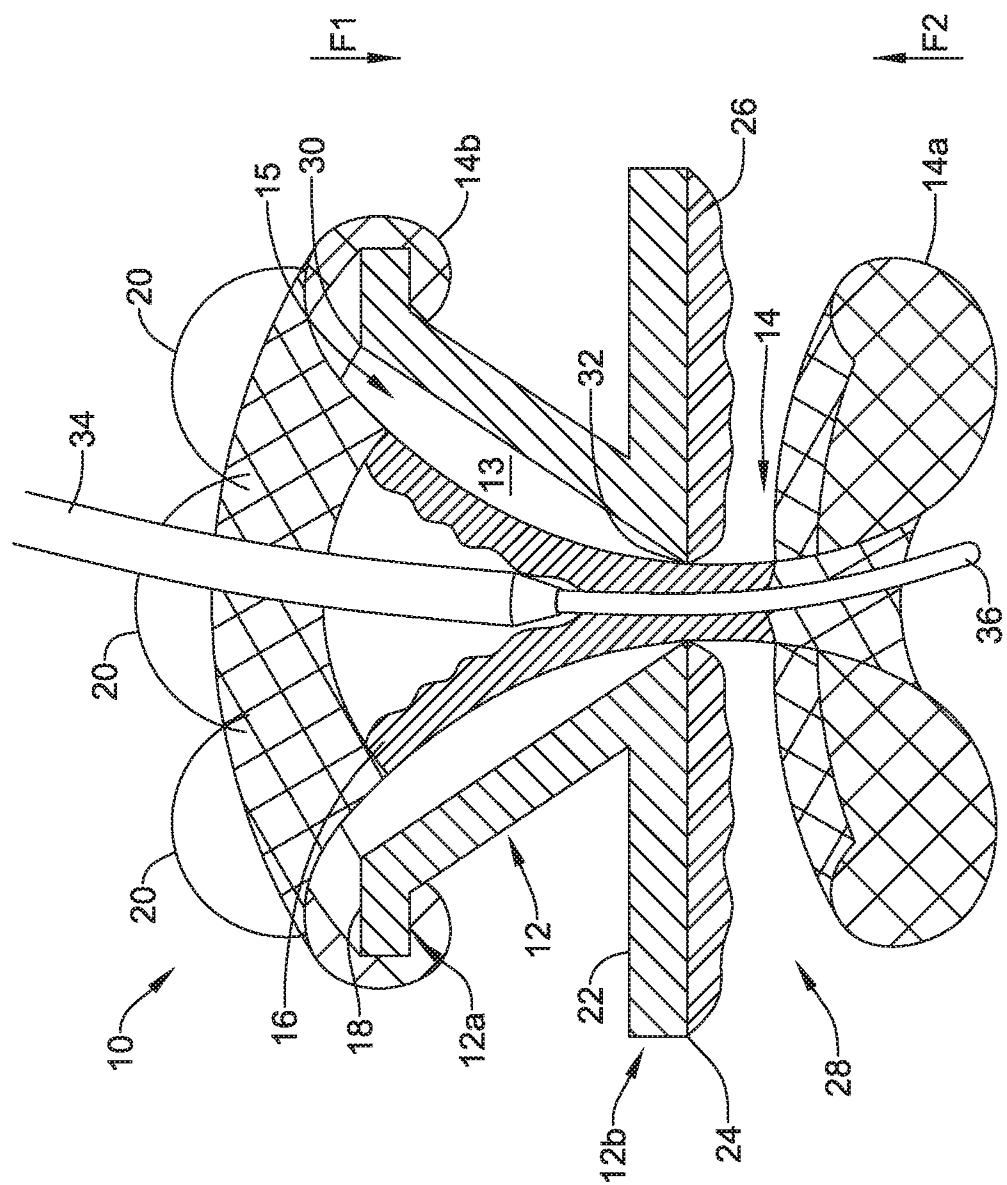
FIG. 6 is a cross-sectional view illustrating an example valve with an example catheter extending through the valve.

FIG. 6 depicts a similar view to the view depicted in FIG. 5, but with a catheter 36 (e.g., a microcatheter or other catheter) opening the valve membrane 16 by applying a positive force to the valve membrane 16. In one example, the catheter 36 may be delivered to the valve 10 via a scope 34 (e.g., an endoscope or other scope) and once the valve 10 is identified using the scope and/or other locating devices or systems, the scope 34 may engage the valve 10 and the catheter 36 may extend out of the scope 34. Once the catheter 36 is extending from the scope 34, the catheter 36 may be moved into position to engage the valve membrane 16 and open the valve 10 as the catheter extends through the valve 10. Once the catheter 36 cross the valve 10, the catheter 36 may be used in a procedure (e.g., an infusion, drainage, and/or other procedure). Although the scope 34 and the catheter 36 are referred to here, other medical devices may be utilized for crossing the valve 10 and/or opening the valve membrane 16.

In some cases, the valve 10 may be configured to deflect force applied to the valve 10 when opening the valve 10 and/or when adjusting a device within the valve 10. In one example, the frame 12 may take on a cone or funnel shaped first portion 12*a* and a disc or extension shaped second portion 12*b*, as discussed above and as shown in FIGS. 5 and 6, which may facilitate deflecting forces applied to the valve 10 as a device (e.g., the catheter 36) engages and/or extends through the valve 10. The valve 10 may be configured to deflect forces applied to the valve in a direction (e.g., an outward direction) away from a target location or puncture site covered by the valve 10. Such deflection of forces by the valve 10 may mitigate a likelihood of tearing the wall at the target location or puncture site.

Figure 7:
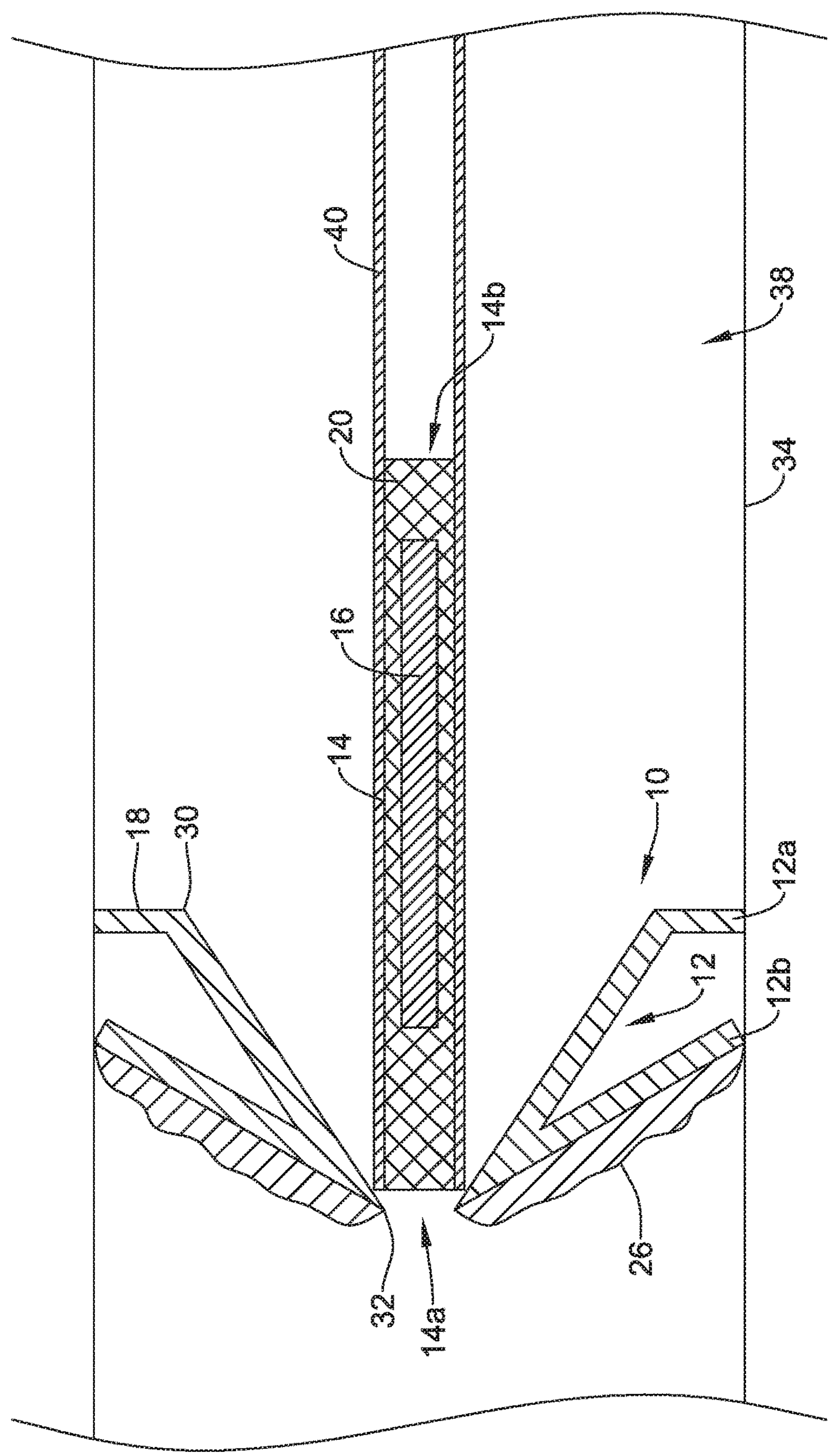
FIG. 7 is a cross-sectional view illustrating an example valve in a delivery configuration within an example scope.

FIG. 7 depicts the valve 10 in a collapsed or delivery configuration. In FIG. 7, the valve 10 is located within a lumen 38 of the scope 34. In the delivery configuration of the valve 10, the second portion 12*b* of the frame 12 may be articulated proximally and the expandable member 14 may be in a cylindrical collapsed configuration within a delivery sheath 40. Once the scope 34 reaches a target location for the valve 10 and a perforation or orifice has been created, the frame 12 may be located against the target location with the second portion 12*b* expanded, the sheath 40 and expandable member 14 may be inserted at least partially through the second opening 32 of the frame 12 and the created perforation or orifice, and the sheath 40 may be withdrawn to allow the expandable member 14 to expand and the valve membrane 16 to seal or close the valve 10 and the created perforation or orifice.

FIGS. 8-13 depict steps in a method of deploying and retrieving the valve 10 from a target location within a stomach (e.g., the stomach 4 or other stomach) of a patient. Although the method of deploying and retrieving the valve 10 is described in the context of the valve 10 being located in a stomach of a patient, other similar procedures may be utilized for deploying and retrieving the valve 10 from a patient's colon and/or from other areas in and around the patient's body.

Endoscopic retrograde cholangiopancreatography (ERCP) is a technique that combines the use of endoscopy and fluoroscopy to diagnose and treat certain problems of the biliary or pancreatic ductal systems. During ERCP, a physician can see, through an endoscope, the inside of a patient's stomach and duodenum, and may inject a contrast medium into the ducts in the biliary tree and pancreas so the biliary tree and pancreas may be seen on radiographs. ERCP may be used primarily to diagnose and treat conditions of the bile ducts and the main pancreatic duct. Endoscopic ultrasound (EUS) or echo-endoscopy is a medical procedure in which endoscopy (e.g., insertion of a probe into a hollow organ) may be combined with ultrasound to obtain images of internal organs in the chest, abdomen, and colon. EUS or echo-endoscopy may be used to visualize the walls of these organs, or to look at adjacent structures. Combined with Doppler imaging, nearby blood vessels may also be evaluated. EUS or echo-endoscopy may be commonly used in the upper digestive tract and in the respiratory system. The valve 10 and the methods of deploying and retrieving the valve 10 disclosed herein may be used in ERCP, EUS, and/or echo-endoscopy procedures, among other procedures.

Figure 8:
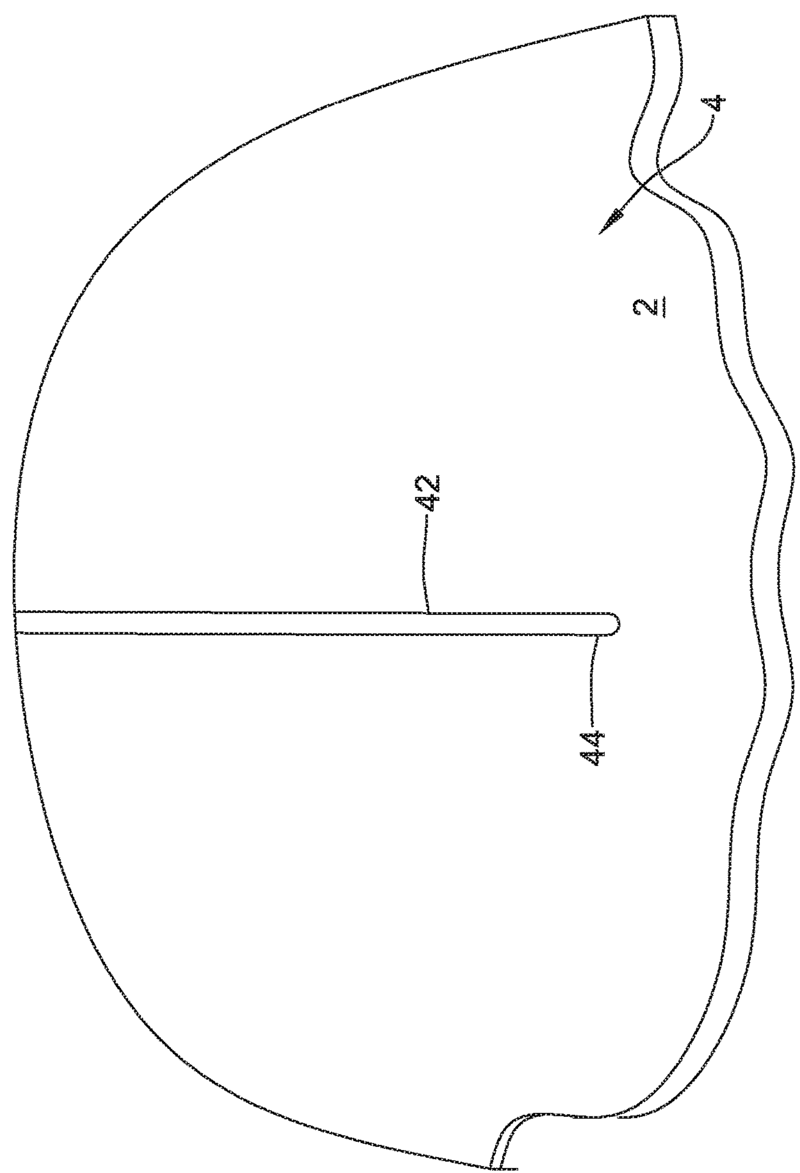
FIGS. 8-13 are various views illustrating steps in an example method of delivering and retrieving a valve.

Once a target location 44 has been identified through imaging from a scope or otherwise, a guide wire 42 may be extended through the wall 2 of a patient to create a perforation or orifice between the stomach and a peritoneal cavity at a target location 44, as shown in FIG. 8. The guide wire 42 may remain extended through the wall 2 of the patient until the valve 10 has been delivered to the target location 44 marked by the location at which the guide wire 42 extends through the wall 2.

Figure 9:
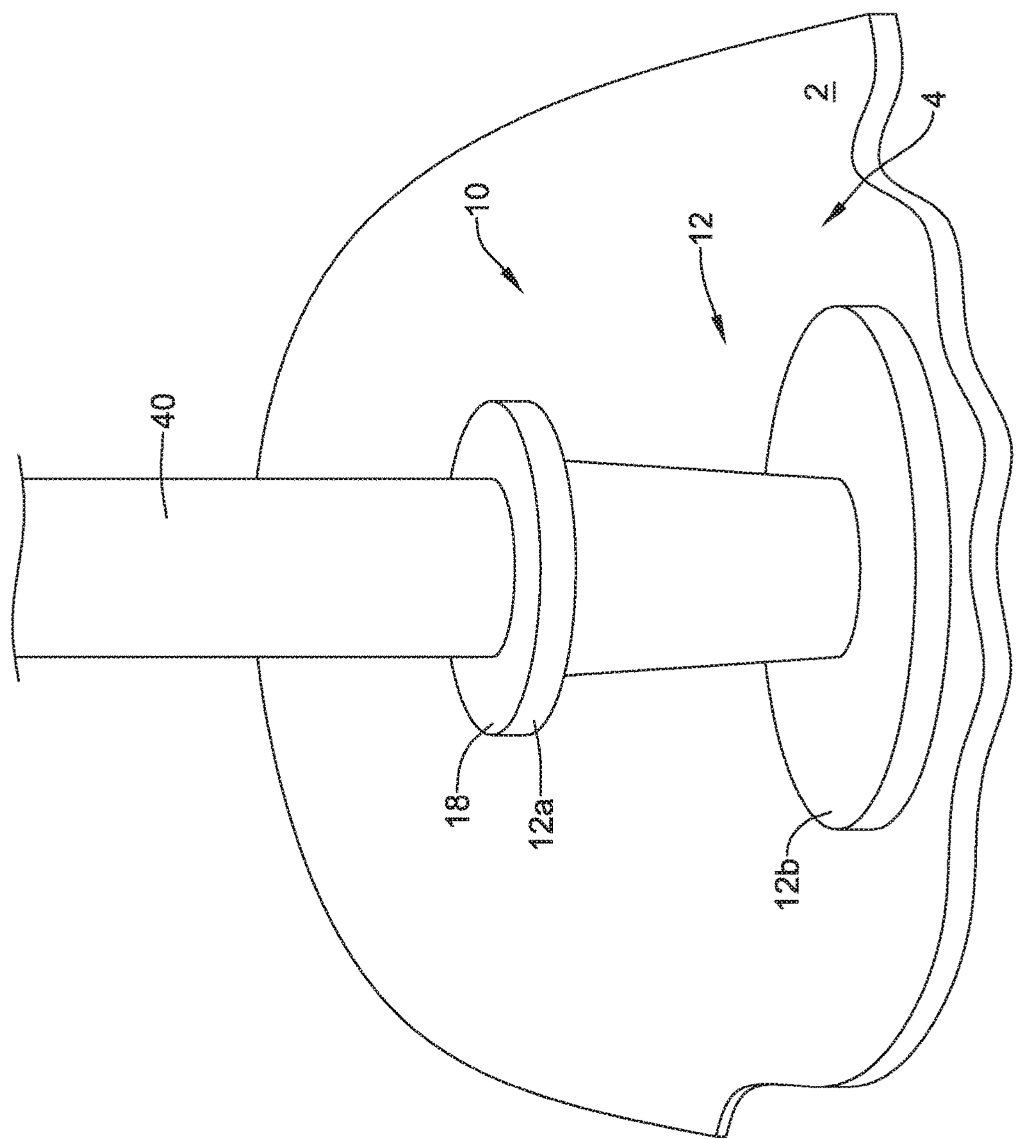

Turning to FIG. 9, the valve 10 may be advanced over the guide wire 42 to the target location (not shown in FIG. 9) and the frame 12 may be positioned adjacent the wall 4 of the patient's stomach, with the base membrane 26 between the second portion 12*b* of the frame and the wall 4 of the patient's stomach to create a seal around the perforation or orifice. As shown in FIG. 9, the second portion may regain its form when delivered from the scope 34 and the second portion 12*b* (e.g., the disc-shaped and/or force distribution portion) may extend radially outward and substantially perpendicular a central longitudinal axis extending through the first portion 12*a* of the frame 12.

Figure 10:
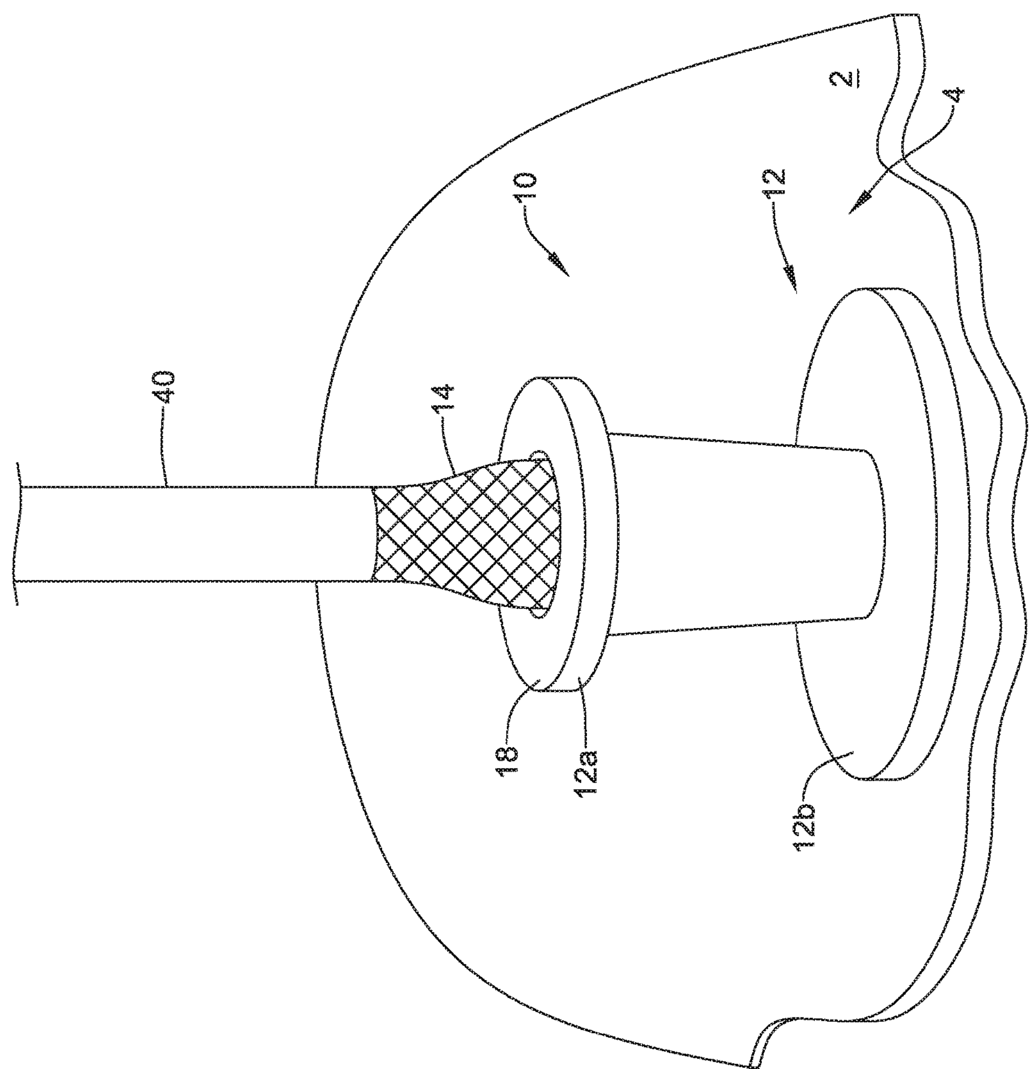

FIG. 10 depicts the withdrawal of the sheath 40 covering the expandable member 14 and the valve membrane 16 from the frame 12 and the valve 10. As the sheath 40 is withdrawn from the valve 10, the expandable member 14 may expand and take its expanded configuration shape.

Figure 11:
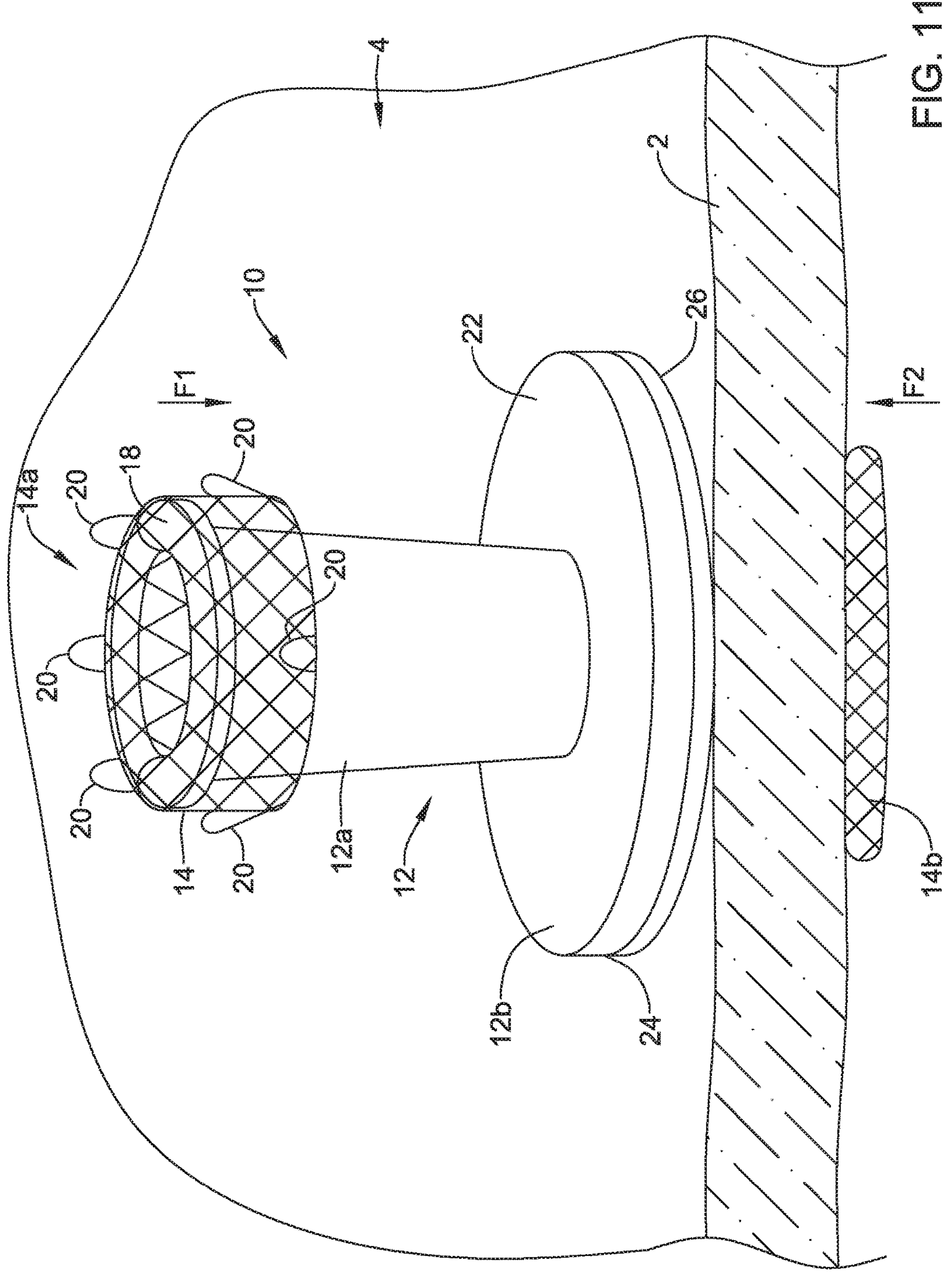

FIG. 11 depicts the valve 10 in the expanded configuration implanted at a target is location on the wall 2 of the stomach of a patient. The implanted valve may be "clipped" or otherwise secured to the wall 2 at the target location due to the first end 14*a* of the expandable member 14 applying a compressive force on the frame 12 in a first axial direction F1 and the second end 14*b* of the expandable member 14 applying a compressive force on the wall 2 in a second axial direction F2 to sandwich the wall 4 between the second end 14*b* of the expandable member 14 and the frame 12. The implanted valve 10 may form a seal between the second portion 12*b* of the frame 12 and the wall 2 via the base membrane 26 sandwiched between the second portion 12*b* of the frame 12 and the wall 2. Further, in the expanded configuration, retrieval members 20 may extend from the expandable member 14 for engagement by a retrieval device.

Figure 12:
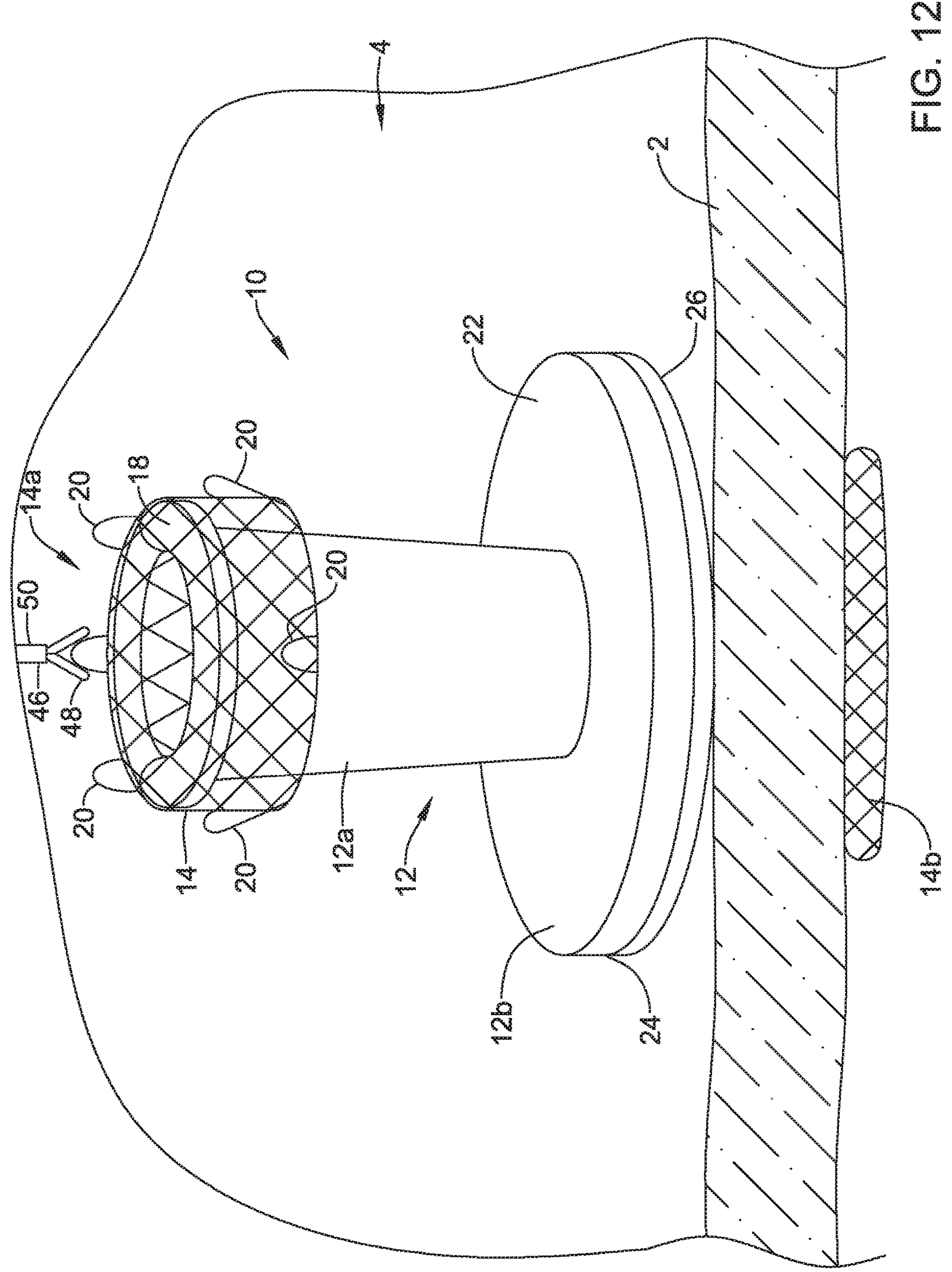

After the valve 10 has been implanted and is no longer needed by the patient, the valve 10 may be retrieved from the target location. FIG. 12 depicts a retrieval device 46 extending to a patient's stomach. In some cases, the retrieval device may include an engaging element 48 extending from an elongated member 50, where the engaging element 48 may be configured to engage one or more of the retrieval members 20 of the valve 10. The engagement element 48 may be any type of engagement element including, but not limited to, opposing jaws (as shown in FIG. 12), a snare, a socket, a hook, and/or one or more other engagement elements configured to engage one or more retrieval members 20.

Figure 13:
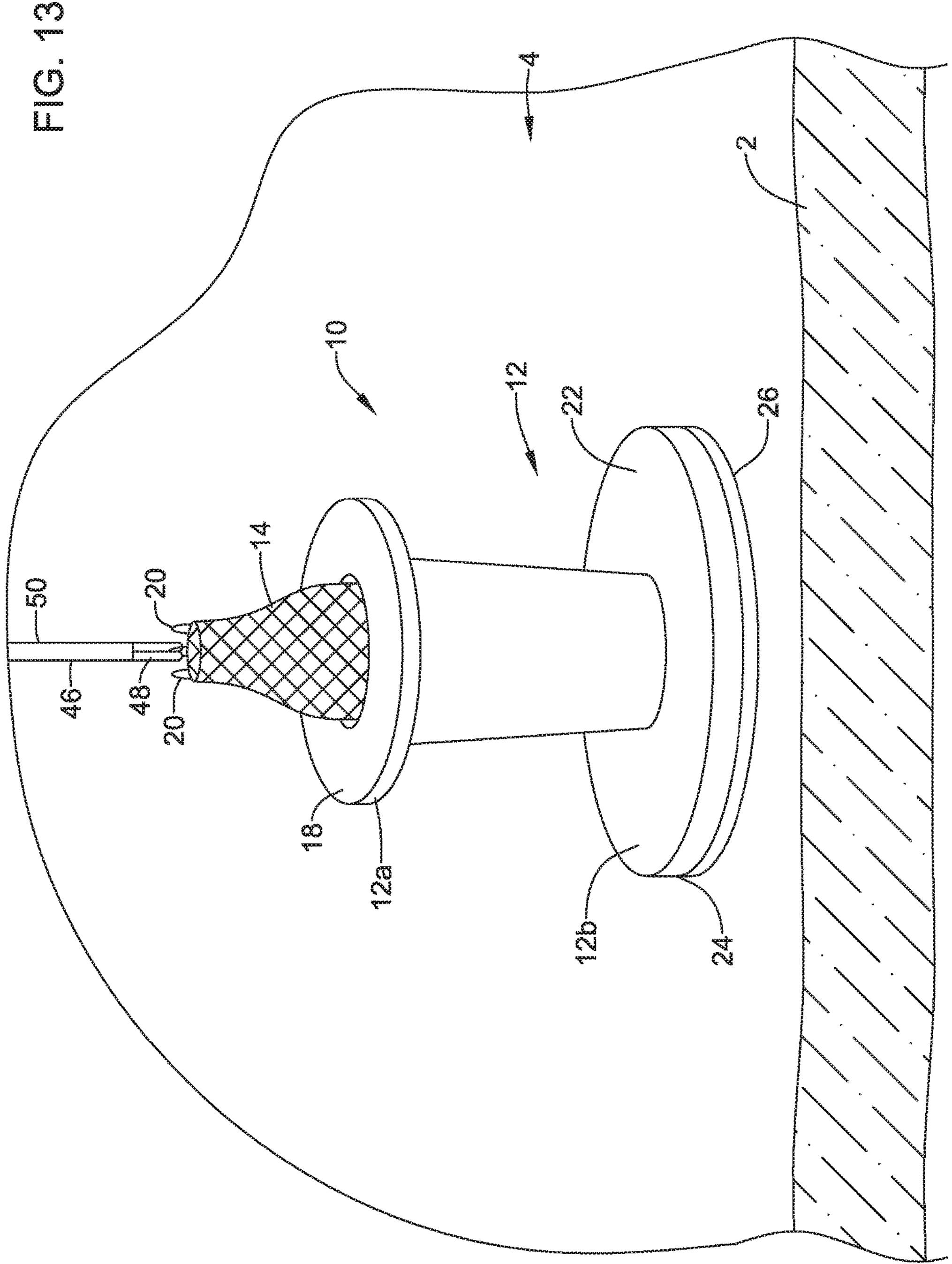

FIG. 13 depicts the retrieval device 46 engaging the retrieval members 20 of the valve 10. Once the retrieval device 46 has engaged one or more retrieval members 20, the retrieval device 46 may be withdrawn along with the valve 10 from the patient's stomach. As the retrieval device 46 is withdrawn, the valve 10 may be removed from the wall 2 of the patient's stomach.

Although not shown, a retrieval sheath may be advanced over the retrieval device 46 to facilitate collapsing the expandable member to its delivery configuration. Further, in some cases, the retrieval device 46 may be extended into a stomach of a patient through an endoscope or other scope and as the retrieval device 46 retracts and retracts the valve 10 from the wall 2, the valve 10 may be received at and/or within the endoscope or other scope.

Additionally, in some case cases, the opening in the wall of the patient that was sealed by the valve 10 may be closed by any closing techniques. For example, the opening may be closed by suturing the opening, applying an adhesive to the opening, fusing the opening, and/or by applying one or more other closing techniques to the opening.

FIGS. 14-18 depict an example method of using the valve implanted in a patient's body. Although the valve 10 is implanted in a patient's stomach in the example depicted in FIGS. 14-18, similar techniques may be used for valves implanted at other areas of the patient's body.

Figure 14:
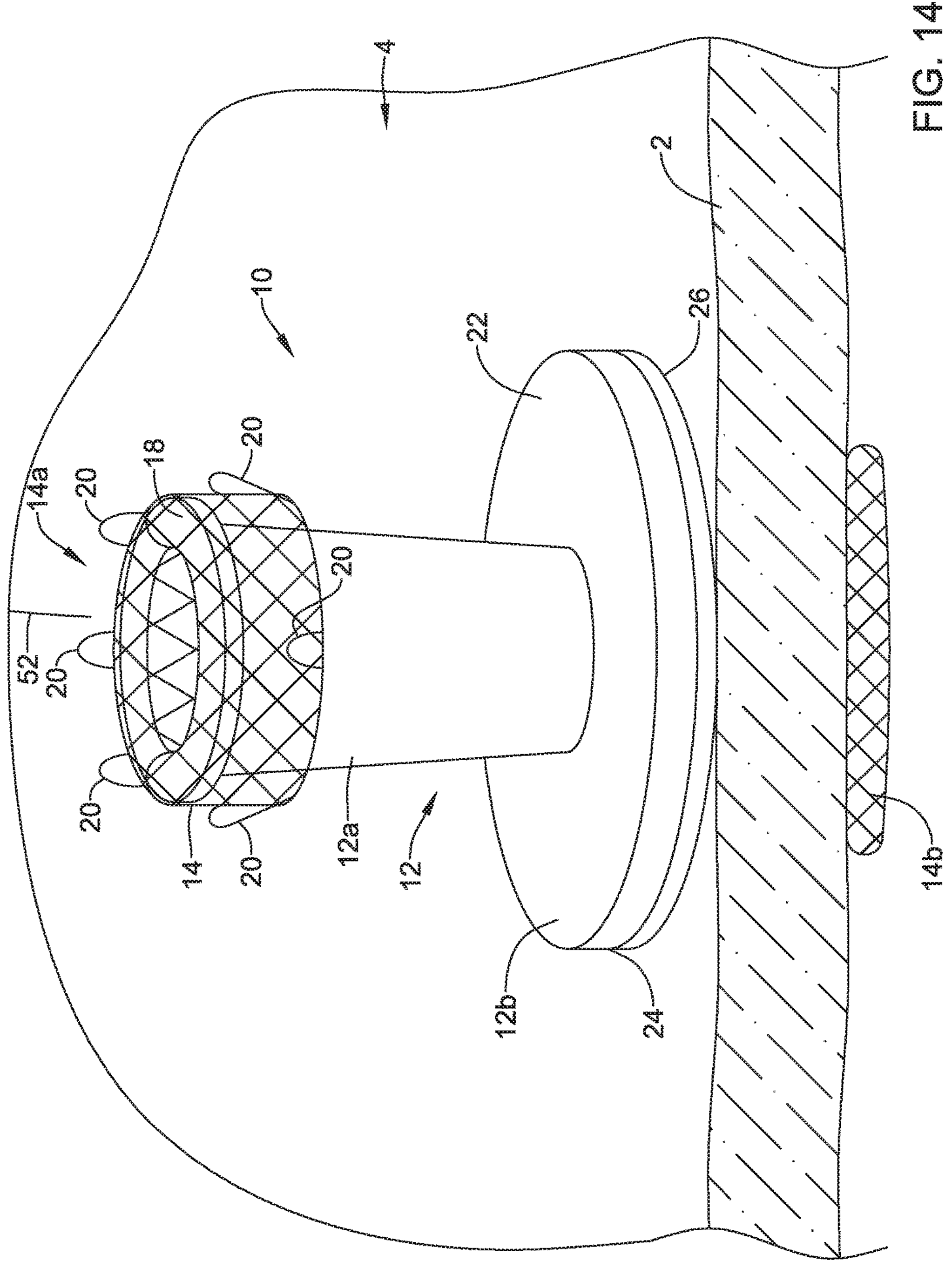
FIGS. 14-18 are various views illustrating steps in an example method of performing a procedure with an implanted valve.
Figure 15:
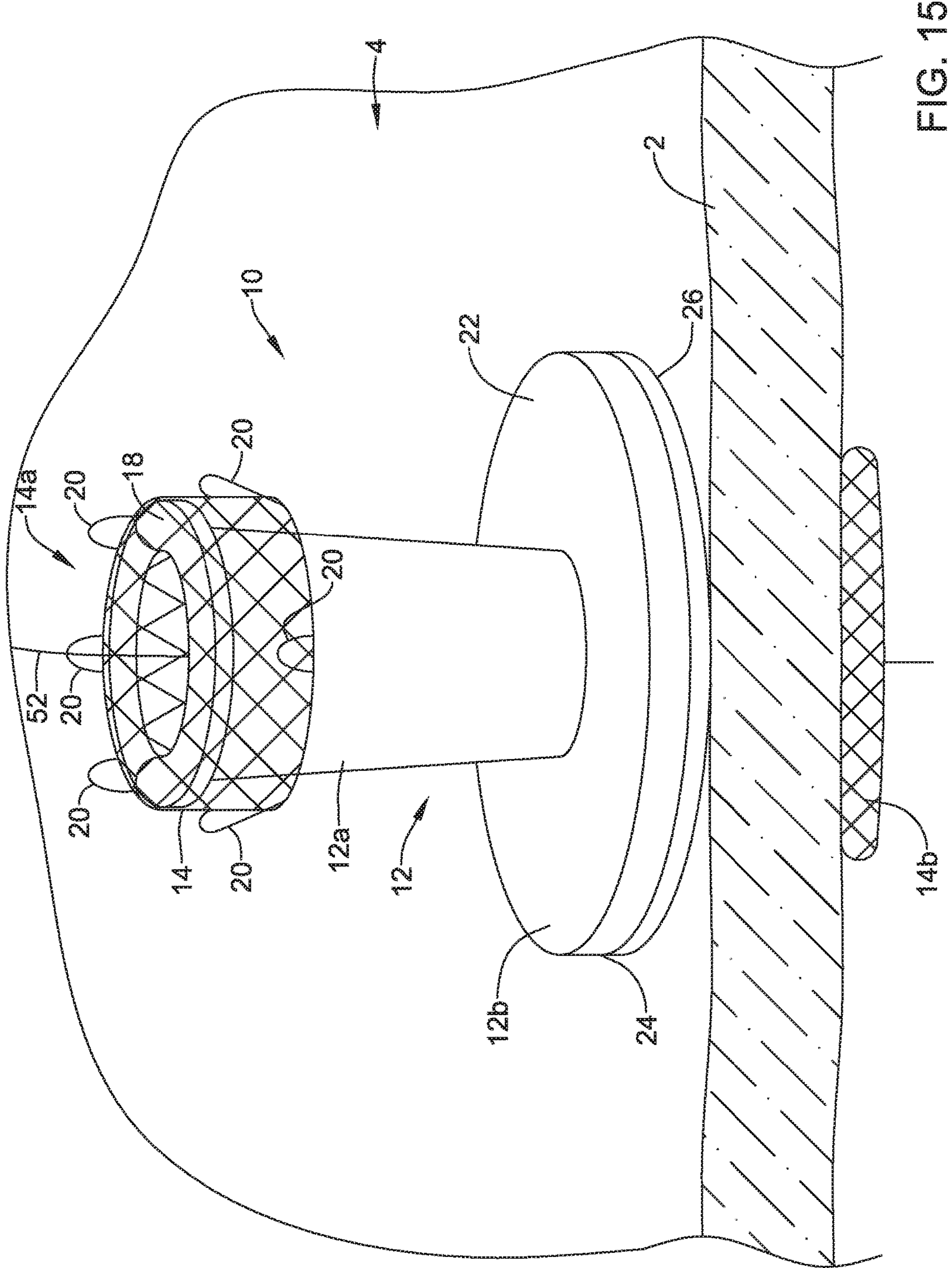

FIG. 14 depicts a guide wire 52 navigating toward the valve 10 implanted on the wall 2 of the patient's stomach. Navigation of the guide wire 52 and/or catheters to the implanted valve 10 may be facilitated with ERCP, EUS, fluoroscopy, and/or other techniques. Once the guide wire 52 reaches the valve 10, the guide wire 52 may be advanced into and/or through the valve membrane 16 of the valve 10 and may cross the wall 2 of the patient's stomach, as shown in FIG. 15. In some cases, the guide wire 52 may cross the wall 2 of the patient's stomach at the initially created perforation or orifice. Alternatively, the guide wire 52 may create a new perforation or orifice in the event the initial perforation or orifice resealed itself. Once the guide wire 52 is advanced into and/or through the valve membrane 16, the valve membrane 16 may seal around the guide wire 52 to prevent leakage through the valve 10.

Figure 16:
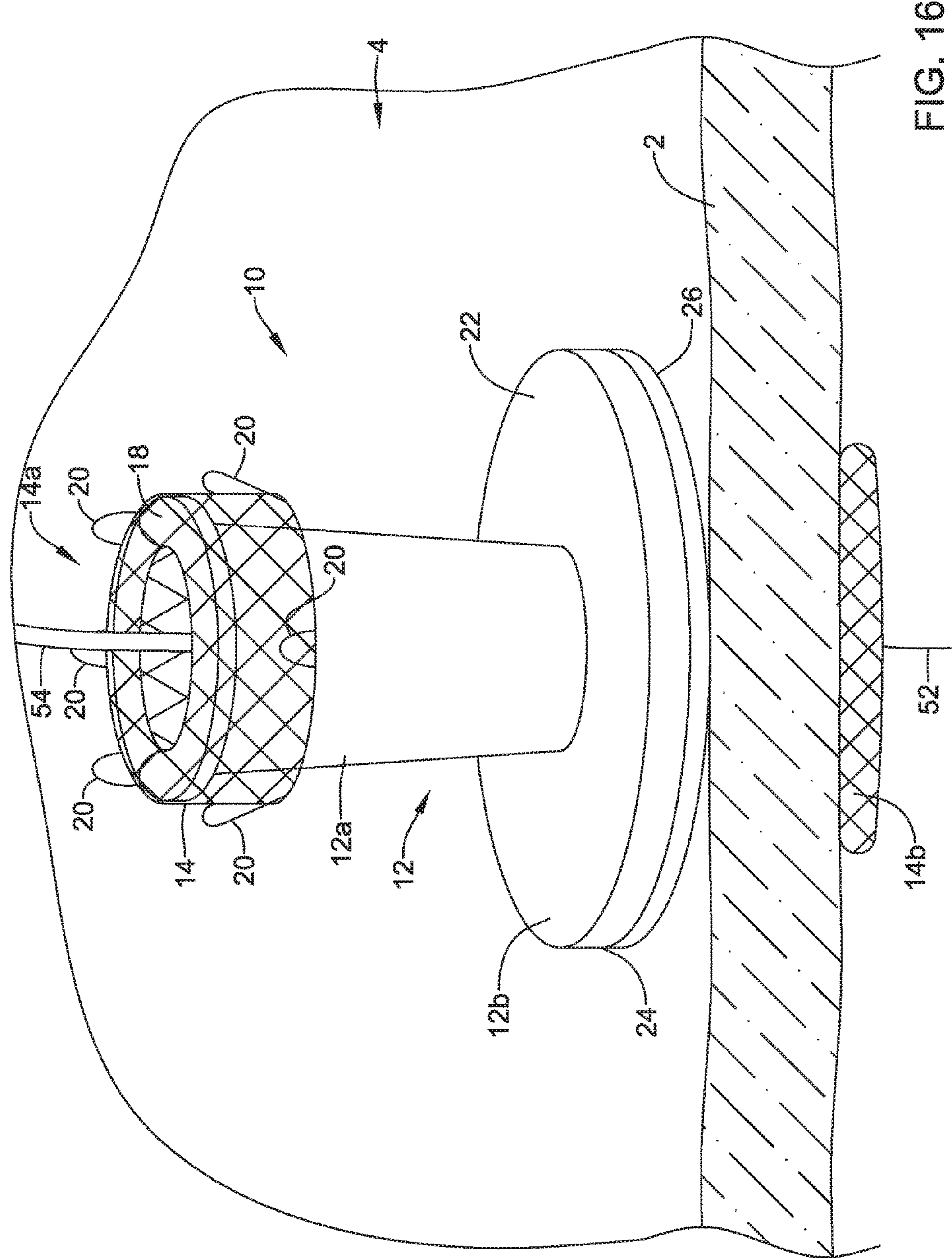
Figure 17:
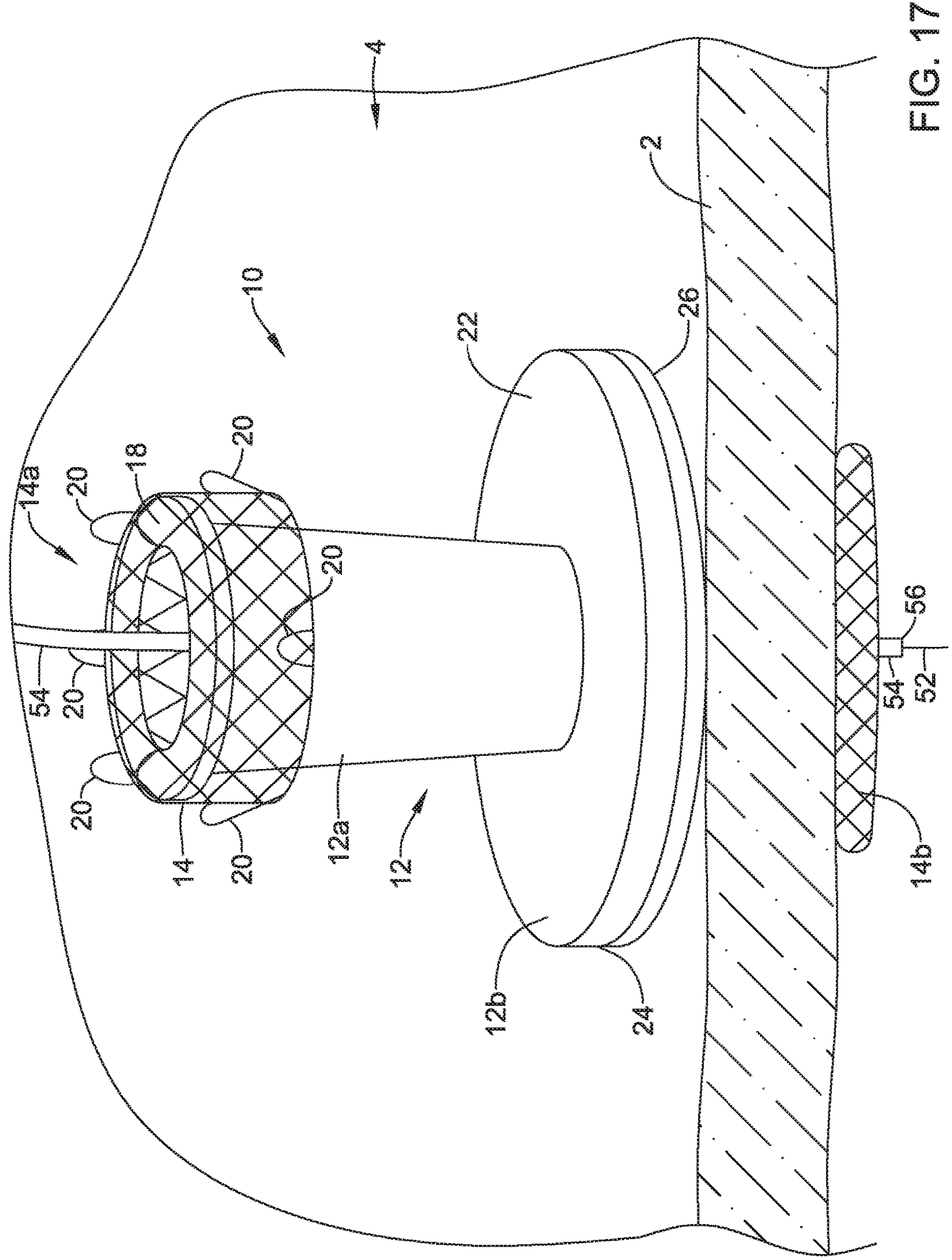
Figure 18:
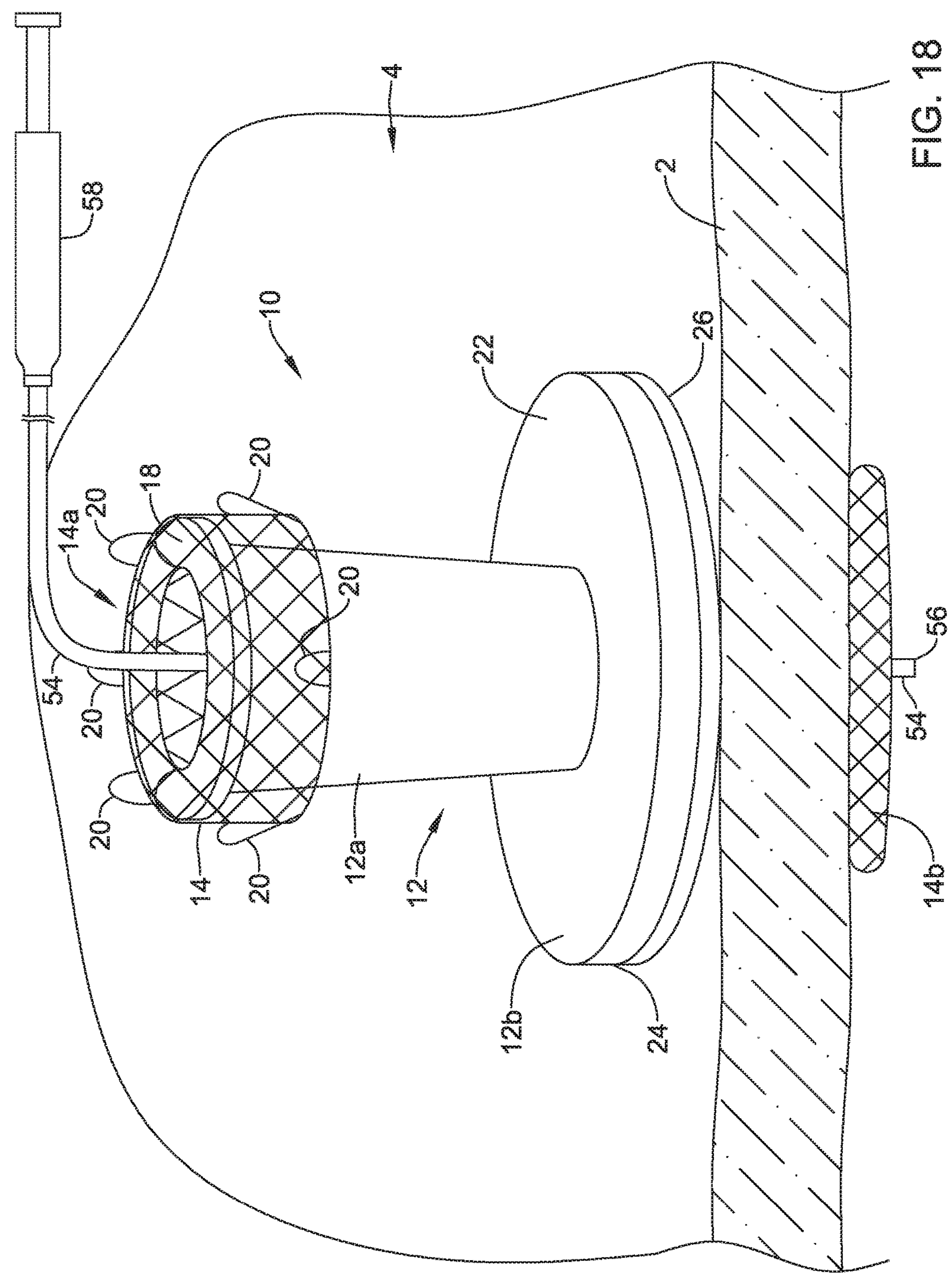

Once the guide wire 52 has crossed the wall 2 of the patient's stomach and has entered the patient's peritoneal cavity, a catheter 54 may be advanced over the guide wire 52, as shown in FIG. 16. Once the catheter 54 reaches the valve 10, the catheter 54 may be advanced into and/or through the valve membrane 16 of the valve 10 and the catheter 54 may cross the wall 2 of the patient's stomach, as shown in FIG. 17. Once the catheter 54 is advanced into and/or through the valve membrane 16, the valve membrane 16 may seal around the catheter 54 to prevent leakage through the valve 10. After the catheter 54 has a distal tip 56 located in the peritoneal cavity 6 of the patient, the guide wire 52 may be withdrawn from the catheter and a physician may perform an infusion procedure (e.g., shown in FIG. 18), a drainage procedure, and/or one or more other procedures. In FIG. 18, a physician is shown infusing fluid from a syringe 58 to the catheter 54 and into the peritoneal cavity 6 of the patient. Although not shown, once is the infusion procedure, drainage procedure, and/or other procedures are completed, the catheter 54 may be withdrawn and the valve membrane 16 may automatically seal the valve 10.

The materials that can be used for the various components of the valve 10 disclosed herein may vary. For simplicity purposes, the following discussion makes reference to frame 12, the expandable member 14, and the valve membrane 16.

However, this is not intended to limit the devices and methods described herein, as the discussion may be applied to other similar members and/or components of valve 10 or components of the delivery systems and procedure systems disclosed herein.

In general, the frame 12, the expandable member 14, and the valve membrane 16 may be made from any suitable method, and may vary depending on the specific material or materials chosen for the frame 12, the expandable member 14, and/or the valve membrane 16. For example, if the frame 12, the expandable member 14, and/or the valve membrane 16 is made from a metal or metal alloy, the frame 12, the expandable member 14, and/or the valve membrane 16 may be formed by photo-etching, laser-cutting, micro-machining, 3D printing, sintering, rolled from flat sheet-stock. However, if the frame 12, the expandable member 14, and/or the valve membrane 16 is made from a polymer material, the frame 12, the expandable member 14, and/or the valve membrane 16 may be made through extrusion and forming techniques.

The frame 12, the expandable member 14, and/or the valve membrane 16 and/or other components of valve 10, the delivery systems, and/or the procedural systems may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available is from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at is body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the frame 12, the expandable member 14, and/or the valve membrane 16 may also be loaded with, made of, or otherwise include a radiopaque material. Radiopaque materials are understood to be materials capable of producing a relatively bright image on a fluoroscopy screen or another imaging technique during a medical procedure. This relatively bright image aids the user of the valve 10 in determining its location. Some examples of radiopaque materials can include, but are not limited to, gold, platinum, palladium, tantalum, tungsten alloy, polymer material loaded with a radiopaque filler (e.g., barium sulfate, bismuth subcarbonate, etc.), and the like.

Additionally, other radiopaque marker bands and/or coils may also be incorporated into the design of the valve 10 to achieve the same result.

In some embodiments, a degree of Magnetic Resonance Imaging (MRI) compatibility is imparted into the valve 10. For example, the frame 12, the expandable member 14, and/or the valve membrane 16 or portions thereof, may be made of a material that does not substantially distort the image and create substantial artifacts (i.e., gaps in the image). Certain ferromagnetic materials, for example, may not be suitable because they may create artifacts in an MRI image. The frame 12, the expandable is member 14, and/or the valve membrane 16, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In at least some embodiments, a sheath (e.g., the sheath 40) or covering (not shown) may be disposed over portions or all of the frame 12, the expandable member 14, and/or the valve membrane 16 that may define a generally smooth outer surface. The sheath may be made from a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers is thereof, polymer/metal composites, and the like. In some embodiments the sheath can be blended with a liquid crystal polymer (LCP). For example, the mixture can contain up to about 6 percent LCP.

In some embodiments, the exterior surface of the frame 12, the expandable member 14, and/or the valve membrane 16 may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the sheath, or in embodiments without a sheath over portion of the frame 12, the expandable member 14, and/or the valve membrane 16, or other portions of the valve 10. Alternatively, the sheath may comprise a lubricious, hydrophilic, protective, or other type of coating. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the to proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

Those skilled in the art will recognize that the present disclosure may be manifested in a variety of forms other than the specific embodiments described and contemplated herein. For instance, as described herein, various embodiments include one or more modules described as performing various functions. However, other embodiments may include additional modules that split the described functions up over more modules than that described herein. Additionally, other embodiments may consolidate the described functions into fewer modules.

Although various features may have been described with respect to less than all embodiments, this disclosure contemplates that those features may be included on any embodiment. Further, although the embodiments described herein may have omitted some combinations of the various described features, this disclosure contemplates embodiments that include any combination of each described feature. Accordingly, departure in form and detail may be made without departing from the scope and spirit of the present disclosure as described in the appended claims.

What is claimed is:

1. An access valve comprising:

a frame having a lumen extending along a length of the frame from a first end of the frame to a second end of the frame;

a self-expandable member extending through the lumen of the frame and having a first end proximal of the first end of the frame and a second end distal of the second end of the frame; and an elastic membrane extending within the self-expandable member, through the lumen and through the second end of the frame to releasably seal the lumen;

wherein the frame is substantially rigid and non-expandable against radial and axial forces acting on the frame from the self-expandable member.

2. The access valve of claim 1, wherein the elastic membrane is secured to the self-expandable member.

3. The access valve of claim 1, wherein:

the self-expandable member has a collapsed configuration and an expanded configuration; and when the self-expandable member is in the expanded configuration, the self-expandable member applies an axially compressive force to the frame.

4. The access valve of claim 1, wherein the frame has an interior surface defining the lumen and the interior surface tapers from the first end to the second end of the frame.

5. The access valve of claim 1, wherein the frame has a conical first portion and a second portion extending radially outward from the conical first portion.

6. The access valve of claim 5, wherein:

the second portion has a first side facing the conical first portion and a second side opposite the first side; and a sealing membrane is secured to the second side of the second portion.

7. The access valve of claim 5, wherein the second portion of the frame is configured to articulate with respect to the conical first portion of the frame.

8. The access valve of claim 1, wherein the elastic membrane comprises a compressible foam.

9. The access valve of claim 1, wherein the self-expandable member is formed from a metal braid.

10. The access valve of claim 1, further comprising:

a retrieval flange connected to the self-expandable member and extending proximal of the frame.

11. A positioning system for positioning an access valve against a bodily wall of a patient, the positioning system comprising:

a delivery sheath;

a valve comprising:

a frame having a first end, a second end, and a lumen extending from the first end to the second end;

a self-expandable member extending through the frame and having a first end proximal of the first end of the frame and a second end distal of the second end of the frame; and an elastic membrane extending within the self-expandable member and through the lumen to releasably seal the lumen; and wherein the delivery sheath is configured to be inserted through the lumen of the frame while covering the self-expandable member to maintain the self-expandable member in a collapsed configuration and is retractable to allow the self-expandable member to expand to an expanded configuration to allow the elastic membrane to releasably seal the lumen.

12. The positioning system of claim 11, further comprising:

a guide wire; and wherein the valve and the delivery sheath extend over the guide wire.

13. The positioning system of claim 11, wherein once the delivery sheath is retracted, the self-expandable member expands radially and axially contracts.

14. The positioning system of claim 11, wherein the valve further comprises a retrieval flange extending proximal of the frame.

15. A method of using an access valve, the method comprising:

advancing a guide wire to a target area on a bodily wall of a patient;

puncturing through the bodily wall of the patient at the target area;

advancing an access valve to the target area;

positioning a frame of the access valve against the bodily wall at the target area;

extending a self-expandable member of the access valve through the frame and the puncture in the bodily wall;

retracting a delivery sheath covering the self-expandable member to allow the self-expandable member to expand to an expanded configuration; and wherein the self-expandable member in the expanded configuration applies axial compressive forces against the bodily wall of the patient and the frame to secure the frame against the bodily wall.

16. The method of claim 15, wherein an elastic membrane of the access valve releasably seals the access valve when the self-expandable member is in the expanded configuration and extending through the frame.

17. The method of claim 16, further comprising:

inserting a catheter into the elastic membrane and advancing the catheter through the elastic membrane to access a distal side of the bodily wall.

18. The method of claim 15, further comprising:

inserting an endoscope into a body cavity at least partially defined by the bodily wall of the patient; and wherein the access valve is advanced through the inserted endoscope to the target area.

19. The method of claim 15, further comprising:

grasping a retrieval flange connected to the self-expandable member and extending proximal of the frame; and withdrawing the self-expandable member into a retrieval sheath to place the self-expandable member in a collapsed configuration for removing the access valve from the patient.

* * * * *